United States Patent
Abad et al.

(10) Patent No.: US 10,889,828 B2
(45) Date of Patent: Jan. 12, 2021

(54) TRANSGENIC PLANTS WITH ENHANCED TRAITS

(71) Applicant: Monsanto Technology LLC, St. Louis, MO (US)

(72) Inventors: Mark S. Abad, Webster Groves, MO (US); Monnanda S. Rajani, Chesterfield, MO (US); Tyamagondlu V. Venkatesh, St. Louis, MO (US); Kammaradi R. Vidya, Bangalore (IN)

(73) Assignee: Monsanto Technology LLC, St. Louis, MO (US)

( * ) Notice: Subject to any disclaimer, the term of this patent is extended or adjusted under 35 U.S.C. 154(b) by 118 days.

(21) Appl. No.: 15/934,237

(22) Filed: Mar. 23, 2018

(65) Prior Publication Data

US 2018/0230482 A1    Aug. 16, 2018

Related U.S. Application Data

(63) Continuation of application No. 14/647,536, filed as application No. PCT/US2013/029245 on Mar. 6, 2013, now abandoned.

(60) Provisional application No. 61/730,765, filed on Nov. 28, 2012.

(51) Int. Cl.
*C12N 15/82* (2006.01)
*C07K 14/415* (2006.01)

(52) U.S. Cl.
CPC ........ *C12N 15/8273* (2013.01); *C07K 14/415* (2013.01); *C12N 15/8218* (2013.01); *C12N 15/8261* (2013.01); *C12N 15/8269* (2013.01); *C12N 15/8271* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 4,761,373 A | 8/1988 | Anderson et al. | |
| 4,810,648 A | 3/1989 | Stalker | |
| 5,013,659 A | 5/1991 | Bedbrook et al. | |
| 5,015,580 A | 5/1991 | Christou et al. | |
| 5,094,945 A | 3/1992 | Comai | |
| 5,107,065 A | 4/1992 | Shewmaker et al. | |
| 5,141,870 A | 8/1992 | Bedbrook et al. | |
| 5,159,135 A | 10/1992 | Umbeck | |
| 5,188,642 A | 2/1993 | Shah et al. | |
| 5,250,515 A | 10/1993 | Fuchs et al. | |
| 5,273,894 A | 12/1993 | Strauch et al. | |
| 5,276,268 A | 1/1994 | Strauch et al. | |
| 5,332,808 A * | 7/1994 | Boston ................ C07K 14/415 435/320.1 |
| 5,378,824 A | 1/1995 | Bedbrook et al. | |
| 5,453,566 A | 9/1995 | Shewmaker et al. | |
| 5,463,174 A | 10/1995 | Moloney et al. | |
| 5,463,175 A | 10/1995 | Barry et al. | |
| 5,538,880 A | 7/1996 | Lundquist et al. | |
| 5,550,318 A | 8/1996 | Adams et al. | |
| 5,552,140 A | 9/1996 | Boston et al. | |
| 5,561,236 A | 10/1996 | Leemans et al. | |
| 5,591,616 A | 1/1997 | Hiei et al. | |
| 5,605,011 A | 2/1997 | Bedbrook et al. | |
| 5,627,061 A | 5/1997 | Barry et al. | |
| 5,633,435 A | 5/1997 | Barry et al. | |
| 5,633,437 A | 5/1997 | Bernasconi et al. | |
| 5,637,489 A | 6/1997 | Strauch et al. | |
| 5,646,024 A | 7/1997 | Leemans et al. | |
| 5,728,925 A | 3/1998 | Herrera-Estrella et al. | |
| 5,759,829 A | 6/1998 | Shewmaker et al. | |
| 5,767,366 A | 6/1998 | Sathasivan et al. | |
| 5,780,708 A | 7/1998 | Lundquist et al. | |
| 5,824,877 A | 10/1998 | Hinchee et al. | |
| 5,846,797 A | 12/1998 | Strickland | |
| 5,880,275 A | 3/1999 | Fischhoff et al. | |
| 5,914,451 A | 6/1999 | Martinell et al. | |
| 5,986,175 A | 11/1999 | Jilka et al. | |
| 6,040,497 A | 3/2000 | Spencer et al. | |
| 6,090,627 A | 7/2000 | Kemp et al. | |
| 6,107,549 A | 8/2000 | Feng et al. | |
| 6,118,047 A | 9/2000 | Anderson et al. | |
| 6,153,812 A | 11/2000 | Fry et al. | |

(Continued)

FOREIGN PATENT DOCUMENTS

| WO | WO2006/073727 | 7/2006 |
|---|---|---|
| WO | WO2008/027592 | 3/2008 |

OTHER PUBLICATIONS

Kawade et al. Differential expression of ribosome-inactivating protein genes during somatic embryogenesis in spinach (*Spinacia oleracea*). Physiologia Plantarum. 2008. 134: 270-281.*

Kodoma et al. eds. Caveat of RNAi in Plants: The Off-Target Effect. RNAi and Plant Gene Function Analysis, Methods in Molecular Biology. 744: pp. 13-25.*

Ying et al. The microRNA (miRNA): Overview of the RNA genes that modulate gene function. Molecular Biotechnology. 2008. 38: 257-268.*

(Continued)

*Primary Examiner* — Ashley K Buran
(74) *Attorney, Agent, or Firm* — Arnold & Porter Kaye Scholer LLP; Lawrence Lavin; David R. Marsh

(57) ABSTRACT

This disclosure provides plants having enhanced traits such as increased yield, increased nitrogen use efficiency and increased water use efficiency: propagules, progeny and field crops of such plants; and methods of making and using such plants. This disclosure also provides methods of producing seed from such plants, growing such seed and selecting progeny plants with the composition, or with enhanced traits. Also disclosed are plants with altered phenotypes which are useful for screening and selecting events for the desired enhanced trait.

19 Claims, No Drawings
Specification includes a Sequence Listing.

(56) References Cited

U.S. PATENT DOCUMENTS

| | | | |
|---|---|---|---|
| 6,160,208 | A | 12/2000 | Lundquist et al. |
| 6,225,105 | B1 | 5/2001 | Sathasivan et al. |
| 6,329,571 | B1 | 12/2001 | Hiei |
| 6,365,807 | B1 | 4/2002 | Christou et al. |
| 6,376,754 | B1 | 4/2002 | Schillinger et al. |
| 6,384,301 | B1 | 5/2002 | Martinell et al. |
| 6,399,861 | B1 | 6/2002 | Anderson et al. |
| 6,414,222 | B1 | 7/2002 | Gengenbach et al. |
| 6,506,599 | B1 | 1/2003 | Yoon |
| 6,613,963 | B1 | 9/2003 | Gingera et al. |
| 6,753,139 | B1 | 6/2004 | Baulcombe et al. |
| 7,026,528 | B2 | 4/2006 | Cheng et al. |
| 7,112,665 | B1 | 9/2006 | Leemans et al. |
| 8,097,710 | B2 | 1/2012 | Baulcombe et al. |
| 8,217,227 | B2 | 7/2012 | Allen et al. |
| 2001/0042257 | A1 | 11/2001 | Connor-Ward et al. |
| 2002/0112260 | A1 | 8/2002 | Schillinger et al. |
| 2002/0192813 | A1 | 12/2002 | Conner et al. |
| 2003/0115626 | A1 | 6/2003 | Weeks et al. |
| 2003/0150017 | A1 | 8/2003 | Mesa et al. |
| 2004/0087030 | A1 | 5/2004 | Armstrong et al. |
| 2004/0106566 | A1 | 6/2004 | Lin et al. |
| 2004/0253604 | A1 | 12/2004 | Lin et al. |
| 2005/0120415 | A1 | 6/2005 | Aukerman |
| 2005/0144669 | A1 | 6/2005 | Rienhart et al. |
| 2006/0174380 | A1 | 8/2006 | Carrington et al. |
| 2006/0200878 | A1 | 9/2006 | Lutfiyya et al. |
| 2007/0124833 | A1 | 5/2007 | Abad et al. |
| 2009/0070898 | A1 | 3/2009 | Allen et al. |
| 2009/0138985 | A1 | 5/2009 | Martinell et al. |
| 2010/0017904 | A1 | 1/2010 | Abad et al. |
| 2011/0061124 | A1 | 3/2011 | Nadzan |
| 2011/0135161 | A1 | 6/2011 | Koutsky et al. |
| 2011/0296555 | A1 | 12/2011 | Ivashuta et al. |
| 2011/0296556 | A1 | 12/2011 | Sammons et al. |

OTHER PUBLICATIONS

Allen et al., microRNA-Directed Phasing during trans-Acting siRNA Biogenesis in Plants, *Cell*, 121:207-221 (2005).

Bartel, MicroRNAs: Genomics, Biogenesis, Mechanism, and Function, *Cell*, 116:281-297 (2004).

Baulcombe, RNA Silencing in Plants, *Nature*, 431:356-363 (2004).

Borsani et al., Endogenous siRNAs Derived from a Pair of Natural cis-Antisense Transcripts Regulate Salt Tolerance in *Arabidopsis*, *Cell*, 123:1279-1291 (2005).

Choe et al., Overexpression of DWARF4 in the Brassinosteroid Biosynthetic Pathway Results in Increased Vegetative Growth and Seed Yield in *Arabidopsis*, *Plant J.*, 26:573-582 (2001).

DeBlock et al., Engineering Herbicide Resistance in Plants by Expression of a Detoxifying Enzyme, *EMBO J.*, 6(9):2513-2518 (1987).

Dugas, et al., MicroRNA Regulation of Gene Expression in Plants, *Curr. Opin. Plant Biol.*, 7:512-520 (2004).

Fraley et al., Expression of Bacterial Genes in Plant Cells, *Proc. Natl. Acad. Sri. USA*, 80:4803-4807 (1983).

GenBank Accession EF519871. *Zea mays* steroid 22-alpha-hydroxylase protein (Dwf4). Published Jun. 7, 2010, pp. 1-2.

Hamilton et al., Two Classes of Short Interfering RNA in RNA Silencing, *EMBO, J.*, 21(17):4671-4679 (2002).

Ingelbrecht et al., Different 3' End Regions Strongly Influence the Level of Gene Expression in Plant Cells, *Plant Cell*, 1:671-680 (1989).

International Search Report and Written Opinion dated Jul. 11, 2013, in International Application No. PCT/US2013/029245.

Klee, et al., Cloning of *Arabidopsis thaliana* gene encoding 5-enolpyruvylshikimate-3-phosphate synthase sequence analysis and manipulation to obtain glyphosate-tolerant plants, *Mol. Gen. Genet.*, 210:437-442 (1987).

Lau et al., Characterization of the piRNA Complex from Rat Testes, *Science*, 313:363-367 (2006).

Liu et al. Expression and Functional Analysis of ZmDWF4, an Ortholog of *Arabidopsis* DWF4 from Maize (*Zea mays* L.)., *Plant Cell Rep.*, 26:2091-2099 (2007).

Lu et al., Genome-wide Analysis for Discovery of Rice microRNAs Reveals Natural Antisense microRNAs (nat-miRNAs), *Proc. Natl. Acad. Sci. USA*, 105: 4951-4956 (2008).

Misawa et al., Functional Expression of the *Erwinia uredovora* Carotenoid Biosynthesis Gene crtI in Transgenic Plants Showing an Increase of β-carotene Biosynthesis Activity and Resistance to the Bleaching Herbicide Norflurazon, *Plant J.*, 4(5):833-840 (1993).

Misawa et al., Expression of an *Erwinia* Phytoene Desaturase Gene not only Confers Multiple Resistance to Herbicides Interfering with Carotenoid Biosynthesis but also Alters Xanthophyll Metabolism in Transgenic Plants, *Plant J.*, 6(4):481-489 (1994).

Murchison et al., miRNAs on the Move: miRNA Biogenesis and the RNAi Machinery, *Curr. Opin. Cell Biol.*, 16:223-229 (2004).

NCBI Reference Sequence NP_200586.1. uncharacterized protein [*Arabidopsis thaliana*]. May 28, 2011. [Retrieved from the internet Jul. 2, 2013: <http://www.ncbi.nlm.nih.gov/protein/15242862?sat=4&satkey=53886512>]; in entirety.

O'Donnell, et al., Mighty Piwis Defend the Germline Against Genome Intruders, *Cell*, 129:37-44 (2007).

Vazquez et al., Endogenous trans-Acting siRNAs Regulate the Accumulation of *Arabidopsis* mRNAs, *Mol. Cell*, 16:69-79 (2004).

Xie et al., Genetic and Functional Diversification of Small RNA Pathways in Plants, *PLoS Biol.*, 2(5):642-652 (2004).

\* cited by examiner

TRANSGENIC PLANTS WITH ENHANCED TRAITS

CROSS REFERENCE TO RELATED APPLICATIONS

This application is a continuation of U.S. application Ser. No. 14/647,536, filed May 27, 2015, which is a U.S. National Phase Application of International Patent Application No. PCT/US2013/028145, filed Mar. 6, 2013, which claims the benefit of under 35USC § 119(e) of U.S. provisional application Ser. No. 61/730,765, filed Nov. 28, 2012, the contents of which are incorporated by reference in their entireties.

INCORPORATION OF SEQUENCE LISTING

The sequence listing file named P34323US02_Seq.txt, which is 50,621 bytes (measured in MS-WINDOWS) and was created on Mar. 22, 2018, is filed herewith and incorporated herein by reference in its entirety.

FIELD OF THE INVENTION

Disclosed herein are plants having enhanced traits such as increased yield, increased nitrogen use efficiency and increased water use efficiency; propagules, progenies and field crops of such plants; and methods of making and using such plants. Also disclosed are methods of producing seed from such plants, growing such seed and/or selecting progeny plants with enhanced traits.

SUMMARY OF THE INVENTION

An aspect of this disclosure provides a plant comprising a recombinant DNA molecule comprising a polynucleotide encoding a polypeptide, wherein the nucleotide sequence of the polynucleotide is selected from the group consisting of: a nucleotide sequence encoding a protein having the amino acid sequence of SEQ ID NO: 2, 4, 6, 8, 10, 12, 14, 16; 23, 24, 25, 26, 27, 28, or 29 and b) a nucleotide sequence encoding a protein with at least 90%, at least 91%, at least 92%, at least 93%, at least 94%, at least 95%, at least 96%, at least 97%, at least 98%, at least 99% identity to SEQ ID NO: 2, 4, 6, 8, 10, 12, 14, 16, 23, 24, 25, 26, 27, 28 or 29; and wherein the plant has at least one enhanced trait as compared to a control plant.

Another aspect of this disclosure also provides a plant comprising a recombinant DNA molecule comprising a polynucleotide, wherein the nucleotide sequence of the polynucleotide is selected from the group consisting of: a) a nucleotide sequence as set forth as SEQ ID NO: 17 or 20; b) a nucleotide sequence that suppresses at least one target gene set forth as SEQ ID NO: 18 or 21; c) a nucleotide sequences that expresses an RNA that suppresses the expression of a protein having the amino acid sequence of SEQ ID NO: 19 or 22; d) a nucleotide sequence with at least 90%, at least 91%, at least 92%, at least 93%, at least 94%, at least 95%, at least 96%, at least 97%, at least 98%, at least 99% identity for SEQ ID NO: 17 or 20; e) a nucleotide sequence with at least 90%, at least 91%, at least 92%, at least 93%, at least 94%, at least 95%, at least 96%, at least 97%, at least 98%, at least 99% identity to SEQ ID NO: 18 or 21; and f) a nucleotide sequence encoding a protein with at least 90%, at least 91%, at least 92%, at least 93%, at least 94%, at least 95%, at least 96%, at least 97%, at least 98%, at least 99% identity to SEQ ID NO: 19 or 22; and wherein the plant has at least one enhanced trait as compared to a control plant.

Another aspect this invention also provides a plant, wherein the plant has at least one enhanced trait as compared to a control plant, and wherein said enhanced trait is selected from the group consisting of increased yield, increased nitrogen use efficiency, and increased water use efficiency.

Yet another aspect of this disclosure provides a plant comprising a recombinant DNA molecule of the disclosure, wherein said plant is a monocot plant or is a member of the family Poaceae, wheat plant, maize plant, sweet corn plant, rice plant, wild rice plant, barley plant, rye, millet plant, sorghum plant, sugar cane plant, turfgrass plant, bamboo plant, oat plant, brome-grass plant, *Miscanthus* plant, pampas grass plant, switchgrass (*Panicum*) plant, and/or teosinte plant, or is a member of the family Alliaceae, onion plant, leek plant, garlic plant, or a member of the family Musaceae, banana plant; or wherein the plant is a dicot plant or is a member of the family Amaranthaceae, spinach plant, *quinoa* plant, a member of the family Anacardiaceae, mango plant, a member of the family Asteraceae, sunflower plant, endive plant, lettuce plant, artichoke plant, a member of the family Brassicaceae, *Arabidopsis thaliana* plant, rape plant, oilseed rape plant, broccoli plant, Brussels sprouts plant, cabbage plant, canola plant, cauliflower plant, kohlrabi plant, turnip plant, radish plant, a member of the family Bromeliaceae, pineapple plant, a member of the family Caricaceae, papaya plant, a member of the family Chenopodiaceae, beet plant, a member of the family Curcurbitaceae, melon plant, cantaloupe plant, squash plant, watermelon plant, honeydew plant, cucumber plant, pumpkin plant, a member of the family Dioscoreaceae, yam plant, a member of the family Ericaceae, blueberry plant, a member of the family Euphorbiaceae, cassava plant, a member of the family Fabaceae, alfalfa plant, clover plant, peanut plant, a member of the family Grossulariaceae, currant plant, a member of the family Juglandaceae, walnut plant, a member of the family Lamiaceae, mint plant, a member of the family Lauraceae, avocado plant, a member of the family Leguminosae, soybean plant, bean plant, pea plant, a member of the family Malvaceae, cotton plant, a member of the family Marantaceae, arrowroot plant, a member of the family Myrtaceae, guava plant, eucalyptus plant, a member of the family Rosaceae, peach plant, apple plant, cherry plant, plum plant, pear plant, prune plant, blackberry plant, raspberry plant, strawberry plant, a member of the family Rubiaceae, coffee plant, a member of the family Rutaceae, citrus plant, orange plant, lemon plant, grapefruit plant, tangerine plant, a member of the family Salicaceae, poplar plant, willow plant, a member of the family Solanaceae, potato plant, sweet potato plant, tomato plant, *Capsicum* plant, tobacco plant, tomatillo plant, eggplant plant, *Atropa* belladona plant, *Datura stramonium* plant, a member of the family Vitaceae, grape plant, a member of the family Umbelliferae, carrot plant; or wherein the plant is a member of the family Pinaceae, cedar plant, fir plant, hemlock plant, larch plant, pine plant, or spruce plant.

Another aspect of this disclosure provides a plant comprising a recombinant DNA molecule of the disclosure, wherein the recombinant DNA molecule further comprises a promoter that is operably linked to the polynucleotide encoding a polypeptide, wherein said promoter is selected from the group consisting of a constitutive, inducible, tissue specific, diurnally regulated, tissue enhanced, and cell specific promoter.

In yet another aspect of this disclosure provides a plant comprising a recombinant DNA molecule of the disclosure, wherein said plant is a progeny, propagule, or field crop. Such field crop is selected from the group consisting of corn, soybean, cotton, canola, rice, barley, oat, wheat, turf grass, alfalfa, sugar beet, sunflower, quinoa and sugar cane.

Yet in another aspect, this disclosure provides a plant comprising a recombinant DNA molecule of the disclosure, wherein said plant is a progeny, propagule, or field crop. Such propagule is selected from the group consisting of a cell, pollen, ovule, flower, embryo, leaf, root, stem, shoot, meristem, grain and seed.

Another aspect of this disclosure provides a method for producing a plant comprising: introducing into a plant cell a recombinant DNA comprising a polynucleotide encoding a polypeptide, wherein the nucleotide sequence of the polynucleotide is selected from the group consisting of: a) a nucleotide sequence encoding a protein having the amino acid sequence of SEQ ID NO: 2, 4, 6, 8, 10, 12, 14, 16, 23, 24, 25, 26, 27, 28 or 29; and b) a nucleotide sequence encoding a protein with at least 90%, at least 91%, at least 92%, at least 93%, at least 94%, at least 95%, at least 96%, at least 97%, at least 98%, at least 99% identity to SEQ ID NO: 2, 4, 6, 8, 10, 12, 14, 16, 23, 24, 25, 26, 27, 28, or 29; and growing a plant from the plant cell.

Another aspect of this disclosure provides a method for producing a plant comprising: introducing into a plant cell a recombinant DNA comprising a polynucleotide, wherein the nucleotide sequence of the polynucleotide suppresses at least one target gene encoding at least one target protein, and wherein the nucleotide sequence is selected from the group consisting of: a) a nucleotide sequence set forth as SEQ ID NO: 17 or 20; b) a nucleotide sequence that suppresses at least one target gene set forth as SEQ ID NO: 18 or 21; c) a nucleotide sequence that suppresses at least one target gene encoding a target protein set forth as SEQ ID NO: 19 or 22; and growing a plant from the plant cell.

Another aspect of this disclosure provides a method of producing a plant comprising: introducing into a plant cell a recombinant DNA molecule of the disclosure; growing a plant from the plant cell. Still another aspect of this disclose further comprises selecting a plant comprising a recombinant DNA molecule of this disclosure, or with at least one enhanced trait selected from increased yield, increased nitrogen use efficiency, and increased water use efficiency as compared to a control plant.

Another aspect of this disclosure provides a method of increasing yield, increasing nitrogen use efficiency, or increasing water use efficiency in a plant comprising: producing a plant comprising a recombinant DNA of the disclosure wherein the plant has an enhanced trait selected from the group consisting of increased yield, increased nitrogen use efficiency, and increased water use efficiency as compared to a control plant; crossing the plant with itself, a second plant from the same plant line, a wild type plant, or a second plant from a different line of plants to produce a seed; growing the seed to produce a plurality of progeny plants, and selecting a progeny plant with increased yield, increased nitrogen use efficiency, or increased water use efficiency.

Yet another aspect of this disclosure provides a plant comprising a recombinant DNA molecule comprising a polynucleotide encoding a polypeptide, wherein the nucleotide sequence of the polynucleotide is selected from the group consisting of: a) a nucleotide sequence encoding a protein having the amino acid sequence of SEQ ID NO: 12, or 16; and b) a nucleotide sequence encoding a protein with at least 90%, at least 91%, at least 92%, at least 93%, at least 94%, at least 95%, at least 96%, at least 97%, at least 98%, at least 99% identity to SEQ ID NO: 12, or 16, wherein the plant has at least one phenotype selected from the group consisting of anthocyanin score, biomass, canopy area, chlorophyll score, plant height, water applied, water content score and water use efficiency that is altered for said plant as compared to a control plant.

Another aspect of this disclosure provides a plant comprising a recombinant DNA molecule comprising a nucleotide sequence, wherein the nucleotide sequence suppresses at least one target gene encoding at least one target protein, and wherein the nucleotide sequence is selected from the group consisting of: a) a nucleotide sequence set forth as SEQ ID NO: 20; b) a nucleotide sequence that suppresses at least one target gene set forth as SEQ ID NO: 21; c) a nucleotide sequence that suppresses at least one target protein set forth as SEQ ID NO: 22; d) a nucleotide sequence with at least 90%, at least 91%, at least 92%, at least 93%, at least 94%, at least 95%, at least 96%, at least 97%, at least 98%, at least 99% identity to SEQ ID NO: 20; e) a nucleotide sequence that suppresses at least one target gene with at least 90%, at least 91%, at least 92%, at least 93%, at least 94%, at least 95%, at least 96%, at least 97%, at least 98%, at least 99% identity to SEQ ID NO: 21; and f) a nucleotide sequence that suppresses at least one target gene encoding a target protein with at least 90%, at least 91%, at least 92%, at least 93%, at least 94%, at least 95%, at least 96%, at least 97%, at least 98%, at least 99% identity to SEQ ID NO: 22, wherein the plant has at least one phenotype selected from the group consisting of anthocyanin score, biomass, canopy area, chlorophyll score, plant height, water applied, water content score and water use efficiency that is altered for said plant as compared to a control plant.

DETAILED DESCRIPTION OF THE INVENTION

In the attached sequence listing:

SEQ ID NOs: 1, 3, 5, 7, 9, 11, 13, and 15 are nucleotide sequences of the coding strand of the DNA molecules used in the recombinant DNA constructs imparting an enhanced trait in plants, each representing a coding sequence for a protein.

SEQ ID NOs: 2, 4, 6, 8, 10, 12, 14, and 16 are amino acid sequences of the cognate proteins of the DNA molecules with nucleotide sequences 1, 3, 5, 7, 9, 11, 13, and 15.

SEQ ID NOs: 17 and 20 are the nucleotide sequences of the suppression elements used to suppress at least one target gene, SEQ ID NOs: 18 and 21, which encode protein SEQ ID NOs: 19 and 22, used in the recombinant DNA constructs to impart an enhanced trait in plants.

SEQ ID NOs: 23-29 are amino acid sequences of homologous proteins.

As used herein, the term "expression" refers to the activity level of a gene in a plant, plant cell or plant tissue in producing a protein. Expression is the process by which information from a gene is used in the synthesis of a functional gene product. Gene expression can give rise to the phenotype. Such phenotypes are often expressed by the synthesis of proteins that control the organism's shape, or that acts as enzymes catalyzing specific metabolic pathways. "Expression or altered expression" in reference to a polynucleotide indicates that the pattern of expression in, for example, a transgenic plant or plant tissue, is different from the expression pattern in a wild-type plant or a non-transgenic plant of the same species. The pattern of expression may also be compared with a reference expression pattern in a wild-type plant of the same species. For example, the polynucleotide or polypeptide is expressed in a cell or tissue type other than a cell or tissue type in which the sequence is expressed in the wild-type plant, or by expression at a time other than at the time the sequence is expressed in the wild-type plant, or by a response to different inducible agents, such as hormones or environmental signals, or at different expression levels (either higher or lower) compared with those found in a wild-type plant. The term also refers to altered expression patterns that are produced by lowering the levels of expression to below the detection level or completely abolishing expression. The resulting expression pattern can be transient or stable, constitutive or inducible. In reference to a polypeptide, the term "ectopic expression or altered expression" can relate to altered activity levels resulting from the interactions of the polypeptides with exogenous or endogenous modulators or from interactions with factors or as a result of the chemical modification of the polypeptides. Variation in expression can occur when, for example, the genes encoding one or more polypeptides are under the control of a constitutive promoter (for example, the cauliflower mosaic virus 35S transcription initiation region). Expression can also be altered by having the gene under the control of an endogenous or a heterologous promoter, or an inducible or tissue specific promoter. Expression can occur throughout a plant, in specific tissues of the plant, or in the presence or absence of particular environmental signals, depending on the promoter used. Expression can also occur in plant cells where endogenous expression of the present polypeptides or functionally equivalent molecules normally occurs, but such normal expression is at a lower level.

The term "overexpression" as used herein refers to a greater expression level of a gene in a plant, plant cell or plant tissue, compared to expression in a wild-type plant, cell or tissue, at any developmental or temporal stage for the gene. Overexpression can occur when, for example, the genes encoding one or more polypeptides are under the control of a promoter (for example, the cauliflower mosaic virus 35S transcription initiation region). Overexpression can also be under the control of a heterologous promoter, or an inducible or tissue specific promoter. Thus, overexpression can occur throughout a plant, in specific tissues of the plant, or in the presence or absence of particular environmental signals, depending on the promoter used. Overexpression can take place in plant cells normally lacking expression of polypeptides functionally equivalent or identical to the present polypeptides. Overexpression can also occur in plant cells where endogenous expression of the present polypeptides or functionally equivalent molecules normally occurs, but such normal expression is at a lower level. Overexpression thus results in a greater than normal production, or "overproduction" of the polypeptide in the plant, cell or tissue.

The term "suppression", as used herein, refers to a lower expression level of a gene in a plant, plant cell or plant tissue, compared to the expression in a wild-type or control plant, cell or tissue, at any developmental or temporal stage for the gene. Suppression can be applied using numerous approaches. Non limiting examples include: to suppress an endogenous gene(s) or a subset of genes in a pathway, to suppress a mutation that has resulted in decreased activity of a protein, to suppress the production of an inhibitory agent, to elevate, reduce or eliminate the level of substrate that an enzyme requires for activity, to produce a new protein; to activate a normally silent gene; or to accumulate a product that does not normally increase under natural conditions.

In one embodiment, RNAi-mediated gene suppression can be used to suppress the expression of targeted genes within plants. In another embodiment, a recombinant DNA construct having a promoter that is functional in a plant cell is operably-linked to a polynucleotide. Thus, when the DNA construct is expressed in a plant cell, the DNA is transcribed into an RNA molecule that suppresses the level of an endogenous protein in the plant cell relative to a control, thereby modulating the regulation of gene expression. In another embodiment, the recombinant DNA construct comprising a polynucleotide sequence is transcribed into an RNA molecule, such an RNA molecule can be a dsRNA processed into siRNAs, a ta-siRNA, which is processed into siRNAs, or a miRNA, all of which target a messenger RNA encoding the protein; and result in the suppression of protein expression relative to a control. The basic mechanisms of RNA silencing are known (See Baulcombe, 2004, Nature 431: 356-363). The main contributors for RNA silencing include, but are not limited to, RNA dependent RNA dsRNA, siRNA, miRNAs, or Dicer and Argonaute nucleases.

Other methods to suppress a gene include, for example, the use of antisense, co-suppression, and RNA interference described in detail in PCT Application Publication No. WO2006073727, which is incorporated herein by reference. Anti-sense gene suppression in plants is described in US Patents Nos. U.S. Pat. Nos. 5,107,065, 5,453,566, and 5,759,829, and are incorporated herein by reference. US Patent Application Publication Nos. US 2004/0106566 and US 2004/0253604, which are incorporated by reference in their entirety herein, disclose methods for inducing gene silencing using nucleic acid constructs containing a gene silencing molecule (sense or anti-sense or both) within an intron flanked by multiple protein-coding exons, wherein, upon splicing and removal of the intron, the protein-coding exons are linked to form a mature mRNA encoding a protein with desired function and the gene silencing molecule is released. Methods of inducing gene silencing using short RNA molecules or DNA constructs encoding short RNA molecules (commonly referred to as "RNAi") as described in U.S. Pat. No. 8,097,710, and methods disclosed for screening for the occurrence of and detecting gene silencing in plants, for example post transcriptional gene silencing as described in U.S. Pat. No. 6,753,139, are incorporated herein by reference. The phased small RNA ("phased sRNA") pathway (see PCT patent application serial No. PCT/US2007/019283, published as WO 2008/027592) is based on an endogenous locus termed a "phased small RNA locus", which transcribes to an RNA transcript forming a single foldback structure that is cleaved in phase in vivo into multiple small double-stranded RNAs (termed "phased small RNAs") capable of suppressing a target gene.

In addition, molecular constructs and methods for use thereof, including constructs including heterologous miRNA recognition sites, constructs for gene suppression including a gene suppression element embedded within an intron flanked on one or on both sides by non-protein-coding sequence, constructs containing engineered miRNA or miRNA precursors, construct for use of inverted repeats for suppression and constructs for suppression of production of mature microRNA in a cell are described in detail in U.S. Pat. No. 8,217,227 and are incorporated herein by reference. The various utilities of miRNAs, their precursors, their recognition sites are described in detail in US Patent Application Publication US 2006/0200878 A1, specifically incorporated by reference herein. Non-limiting examples of these utilities include: (1) the expression of a native miRNA or miRNA precursor sequence to suppress a target gene; (2) the expression of an engineered (non-native) miRNA or miRNA precursor sequence to suppress a target gene; (3) the expression of a transgene with a miRNA recognition site, wherein the transgene is suppressed when the corresponding mature miRNA is expressed, either endogenously or transgenically; (4) the expression of a transgene driven by a miRNA promoter; and (5) the expression of a transgene with an RNA molecule, wherein a RNA molecule is a cleavage blocker of a miRNA or is a miRNA decoy of a miRNA (Examples of such RNAi-mediated gene suppression approaches are disclosed in U.S. Patent Application Publication No. 2009/61288019 and incorporated herein by reference). Additionally MIR genes and mature miRNAs are also described in US Patent Application Publication Nos. US 2005/0120415 and US 2005/0144669 A1, which is incorporated by reference herein. MIR genes have been reported to occur in inter-genic regions, both isolated and in clusters in the genome, but can also be located entirely or partially within introns of other genes (both protein-coding and non-protein-coding).

A method described in US Patent Application Publication No. US 2011/0296556 A1, herein incorporated by reference, discloses how to modulate gene expression in plants by using external application of polynucleotide molecules. The method provides for an RNA or DNA containing composition for the regulation of plant gene expression when the composition is applied to a plant surface.

As used herein "microRNAs" (miRNAs) are non-protein coding RNAs, generally of between about 19 to about 25 nucleotides (generally of between about 19 to about 25 nucleotides but commonly about 20-24 nucleotides in plants), that guide cleavage in trans of target transcripts, negatively regulating the expression of genes involved in various regulation and development pathways (See Bartel (2004) Cell, 116:281-297). In some cases, miRNAs serve to guide in-phase processing of siRNA primary transcripts (see Allen et al. (2005) Cell, 121:207-221, which is incorporated herein by reference). Micro RNAs are regulatory miRNAs that can also control gene expression at the level of translation and maintain mRNA stability in the cytoplasm. Recombinant DNA constructs can be used to modify the activity of native miRNAs by a variety of means. By increasing the expression of a miRNA, for example, temporally or spatially, the modulation of expression of a native target gene can be enhanced. An alternative gene suppression approach for suppressing the expression of a target protein can include the use of a recombinant DNA construct that produces a synthetic miRNA that is designed to bind to a native or synthetic miRNA recognition site on messenger RNA for the target protein. Alternatively, by reducing the expression of a miRNA, the modulation of a native target gene can be diminished resulting in enhanced expression of the target protein. More specifically, the expression of a target protein can be enhanced by suppression of the activity of the miRNA that binds to a recognition site in the messenger RNA that is transcribed from the native gene for the target protein. Several types of recombinant DNA constructs can be designed to suppress the activity of a miRNA. Recombinant DNA encoding an RNA encoding a miRNA, or a miRNA-sensitive RNA are designed using methods disclosed in US Patent Application Publication No. US 2009/0070898 A1. The construction and description of such recombinant DNA constructs is disclosed in US Patent Application Publication No. US 2009/0070898 A1, and US application publication No. US 2011/0296555 A1, all of which are incorporated herein by reference.

As used herein, "double-stranded RNA" ("dsRNA") is RNA capable of being processed through an RNAi pathway (for example, to produce small interfering RNAs or microRNAs, see, for example, Xie et al. (2004) PLoS Biol., 2:642-652; Bartel (2004) Cell, 116:281-297; Murchison and Hannon (2004) Curr. Opin. Cell Biol., 16:223-229; and Dugas and Bartel (2004) Curr. Opin. Plant Biol., 7:512-520, all of which are incorporated by reference. The transcribable DNA that is processed into dsRNA can be flanked on one or both sides by DNA that transcribes to RNA capable of forming dsRNA (for example, by forming an inverted repeat where the transcribable DNA is located in the middle "spacer" region, or by forming separate dsRNA regions on one or both sides of the transcribable DNA, which may be processed to small interfering RNAs, to microRNA precursors such as pre-miRNAs, or to mature microRNAs).

As used herein, "siRNA" refers to the siRNA pathway involves the non-phased cleavage of a longer double-stranded RNA intermediate to small interfering RNAs ("siRNAs"). The size of siRNAs can be in a range from about 19 to about 25 base pairs, but common classes of siRNAs include those containing 21 base pairs or 24 base pairs. See, for example, Hamilton et al. (2002) EMBO J., 21:4671-4679. siRNAs are typically associated with posttranscriptional gene silencing triggered by transgenes and viruses in plants.

As used herein "trans-acting RNAs" ("ta-siRNA") refer to miRNAs that serve to guide in-phase processing of siRNA primary transcripts in a process that requires an RNA-dependent RNA polymerase for production of a double-stranded RNA precursor; trans-acting siRNAs are defined by lack of secondary structure, a miRNA target site that initiates production of double-stranded RNA, requirements of DCL4 and an RNA-dependent RNA polymerase (RDR6), and production of multiple phased ~21-nt small RNAs with matched duplexes with 2-nucleotide 3' overhangs (see Allen et al. (2005) Cell, 121:207-221; Vazquez et al. (2004) Mol. Cell, 16:69-79).

As used herein, "noncoding RNAs" ("ncRNAs") are another class of RNAs that have functional roles in regulating gene expression in higher cells. Small RNAs have chain lengths varying from approximately 60-300 nucleotides in length. Small nuclear RNAs (snRNAs) can exist as a complex tightly bound to one or more proteins in particles termed small nuclear ribonucleoproteins (snRNPs). Some occupy the nucleoplasm, which contains the DNA and devotes to the production of mRNAs for export to the cytoplasm. Others occupy the nucleolus, the location where ribosomes are assembled prior to being directed to the cytoplasm for protein synthesis.

As used herein, "natural anti-sense transcript small interfering RNA" ("nat-siRNA") refers to gene suppression mediated by small RNAs processed from natural antisense transcripts are involved in at least two pathways. In the natural antisense transcript small interfering RNA ("nat-siRNA") pathway (Borsani et al. (2005) Cell, 123:1279-1291), siRNAs are generated by DCL1 cleavage of a double-stranded RNA formed between the antisense transcripts of a pair of genes (cis-antisense gene pairs). A similar natural anti-sense transcript microRNA ("nat-miRNA") pathway (Lu et al. (2008) Proc. Natl. Acad. Sci. USA, 105: 4951-4956) has also been reported. In metazoan animals, small RNAs termed Piwi-interacting RNAs ("piRNAs") also have gene-silencing activity (See Lau et al. (2006) Science, 313:363-367; O'Donnell & Boeke (2007) Cell, 129:37-44).

Small RNAs that regulate protein expression can include miRNAs and ta-siRNAs. A miRNA is a small (typically about 21 nucleotide) RNA that has the ability to modulate the expression of a target gene by binding to messenger RNA for the target protein leading to destabilization of the target protein messenger RNA or translational inhibition of the target protein messenger RNA, resulting in reduction of the target protein. The design and construction of ta-siRNA constructs and their use in the modulation of protein in transgenic plant cells was disclosed by Allen and Carrington in US Patent Application Publication No. US 2006/0174380 A1 which is incorporated herein by reference. The expression or suppression of such small RNAs are aspects of the invention illustrated by reference the use of miRNAs.

As used herein, "inverted repeat" ("IR") is a sequence of nucleotides that is the reversed complement of another sequence further downstream. For example, 5'---GACTGC . . . GCAGTC---3'. When no nucleotides intervene between the sequence and its downstream complement, it is called a palindrome. Inverted repeats define the boundaries in transposons. Inverted repeats also indicate regions capable of self-complementary base pairing (regions within a single sequence which can base pair with each other).

As used herein, "miRNA decoy" refers to a sequence that can be recognized and bound by an endogenous mature miRNA resulting in base-pairing between the miRNA decoy sequence and the endogenous mature miRNA, thereby forming a cleavage-resistant RNA duplex that is not cleaved because of the presence of mismatches between the miRNA decoy sequence and the mature miRNA. Prediction or designing of a miRNA decoy sequence have been described in US Patent Application Publication No. US 2009/0070898 A1.

As used herein, "RNA cleavage blocker" is the RNA including single-stranded RNA that binds to the transcript of at least one target gene, and more specifically refers to the portion(s) of the single-stranded RNA that forms a hybridized segment of at least partially double-stranded RNA with the transcript. Cleavage blockers inhibit double-stranded RNA-mediated suppression of the at least one target gene, thereby increasing expression of the target gene (relative to expression in the absence of the cleavage blocker). The RNA includes single-stranded RNA that binds to the transcript of at least one target gene to form a hybridized segment of at least partially double-stranded RNA that imparts to the transcript resistance to cleavage by an RNase III ribonuclease within or in the vicinity of the hybridized segment, wherein the binding of the single-stranded RNA to the transcript (and the resultant formation of the hybridized segment) inhibits double-stranded RNA-mediated suppression of the at least one target gene.

As used herein, "target gene" include any gene for which expression is intended to be modified, either in a cell containing the recombinant DNA construct or in other cells or organisms that come into contact with the recombinant DNA construct. The target gene can be native (endogenous) to the cell (for example, a cell of a plant or animal) in which the recombinant DNA construct is transcribed, or can be native to a pest or pathogen (or a symbiont of the pest or pathogen) of the plant or animal in which the recombinant DNA construct is transcribed. The target gene can also be an exogenous gene, such as a transgene in a plant. A target gene can be a native gene targeted for suppression, with or without concurrent expression of an exogenous transgene. For example, by including a gene expression element in the recombinant DNA construct, or in a separate recombinant DNA construct. The recombinant DNA construct can be designed to be more specifically modulate the expression of the target gene. For example, by designing the recombinant DNA construct to include DNA that is processed to an RNA including single-stranded RNA that binds to the target gene transcript, wherein the single-stranded RNA includes a nucleotide sequence substantially non-identical (or non-complementary) to a non-target gene sequence (and is thus less likely to bind to a non-target gene transcript). Alternatively, non-target genes can include any gene for which expression is not intended to be modified, either in a cell containing the recombinant DNA construct or in other cells or organisms that come into contact with the recombinant DNA construct.

As used herein, "target sequence" is the sequence suppress the expression of a protein encoded by a target gene endogenous or exogenous to a plant. The target sequence can include nucleotide sequence to target for suppression gene of interest (for example an mRNA encoding a protein), or a sequence that is targeted by an RNA that is designed and processed to an siRNA or miRNA. The target sequence can be translatable (coding) sequence, or can be non-coding sequence (such as non-coding regulatory sequence), or both. The target sequence can include at least one eukaryotic target sequence, at least one non-eukaryotic target sequence, or both. A target sequence can include any sequence from any species (including, but not limited to, non-eukaryotes such as bacteria, and viruses; fungi; plants, including monocots and dicots, such as crop plants). The recombinant DNA construct can be designed to more specifically modulate the expression of the target gene, for example, by designing the recombinant DNA construct to include DNA that is processed to an RNA including single-stranded RNA that binds to the target gene transcript, wherein the single-stranded RNA includes a nucleotide sequence substantially non-identical (or non-complementary) to a non-target gene sequence (and is thus less likely to bind to a non-target gene transcript).

In one embodiment, the modulation of protein in transgenic plant cells can be achieved by a variety of approaches involving the use of recombinant DNA constructs. None limiting examples of such recombinant DNA constructs include recombinant DNA constructs that produce messenger RNA for the target protein where native miRNA recognition sites in the mRNA for the target protein are modified or deleted, recombinant DNA constructs that produce an RNA gene suppression element such as a miRNA or a dsRNA comprising sense and anti-sense sequences from the gene encoding the target protein, recombinant DNA constructs that produce a transacting short interfering RNA (ta-siRNA) and recombinant DNA constructs that produce a miRNA element such as a decoy miRNA that is a target for native miRNA or RNA that sequesters target messenger RNA away from native miRNA.

As used herein, "gene suppression elements" refer to a genetic element(s) that can be transcribable DNA of any suitable length, and will generally include at least about 19 to about 27 nucleotides (for example 19, 20, 21, 22, 23, or 24 nucleotides) for every target gene that the recombinant DNA construct is intended to suppress. In one embodiment, the gene suppression element includes more than 23 nucleotides (for example, more than about 30, about 50, about 100, about 200, about 300, about 500, about 1000, about 1500, about 2000, about 3000, about 4000, or about 5000 nucleotides) for every target gene that the recombinant DNA construct is intended to suppress.

In another embodiment, gene suppression elements refer to, but are not limited to, elements that include transcribable exogenous DNAs: DNA that includes at least one anti-sense DNA segment to at least one segment of the at least one target gene, or DNA that includes multiple copies of at least one anti-sense DNA segment that is anti-sense to at least one segment of the at least one target gene; DNA that includes at least one sense DNA segment that is at least one segment of the at least one target gene, or DNA that includes multiple copies of at least one sense DNA segment that is at least one segment of the at least one target gene; DNA that transcribes to RNA for suppressing at least one target gene by forming double-stranded RNA and includes at least one anti-sense DNA segment that is anti-sense to at least one segment of the at least one target gene and at least one sense DNA segment that is at least one segment of the at least one target gene; DNA that transcribes to RNA for suppressing the at least one target gene by forming a single double-stranded RNA and includes multiple serial anti-sense DNA segments that are anti-sense to at least one segment of the at least one target gene and multiple serial sense DNA segments that are at least one segment of the at least one target gene; DNA that transcribes to RNA for suppressing the at least one target gene by forming multiple double strands of RNA and includes multiple anti-sense DNA segments that are anti-sense to at least one segment of the at least one target gene and multiple sense DNA segments that are at least one segment of the at least one target gene, and wherein said multiple anti-sense DNA segments and the multiple sense DNA segments are arranged in a series of inverted repeats; and DNA that includes nucleotides derived from a miRNA, or DNA that includes nucleotides of a siRNA. Various arrangements of double-stranded RNA (dsRNA) that can be transcribed from embodiments of the gene suppression elements and transcribable exogenous DNAs and can suppress one or more target genes, and can form a single double-stranded RNA or multiple double strands of RNA, or a single dsRNA "stem" or multiple "stems". In some embodiments, an intron is used to deliver a gene suppression element in the absence of any protein-coding exons (coding sequence). In a non-limiting example, an intron, such as an expression-enhancing intron, is interrupted by embedding within the intron a gene suppression element, wherein, upon transcription, the gene suppression element is excised from the intron. Additional gene suppression elements are described in detail in US Patent Application Publication No. US 2006/0200878 A1, which disclosure is specifically incorporated herein by reference, and include one or more of: (a) DNA that includes at least one anti-sense DNA segment that is anti-sense to at least one segment of the gene to be suppressed; (b) DNA that includes multiple copies of at least one anti-sense DNA segment that is anti-sense to at least one segment of the gene to be suppressed; (c) DNA that includes at least one sense DNA segment that is at least one segment of the gene to be suppressed; (d) DNA that includes multiple copies of at least one sense DNA segment that is at least one segment of the gene to be suppressed; (e) DNA that transcribes to RNA for suppressing the gene to be suppressed by forming double-stranded RNA and includes at least one anti-sense DNA segment that is anti-sense to at least one segment of the gene to be suppressed and at least one sense DNA segment that is at least one segment of the gene to be suppressed; (f) DNA that transcribes to RNA for suppressing the gene to be suppressed by forming a single double-stranded RNA and includes multiple serial anti-sense DNA segments that are anti-sense to at least one segment of the gene to be suppressed and multiple serial sense DNA segments that are at least one segment of the gene to be suppressed; (g) DNA that transcribes to RNA for suppressing the gene to be suppressed by forming multiple double strands of RNA and includes multiple anti-sense DNA segments that are anti-sense to at least one segment of the gene to be suppressed and multiple sense DNA segments that are at least one segment of the gene to be suppressed, and wherein the multiple anti-sense DNA segments and the multiple sense DNA segments are arranged in a series of inverted repeats; (h) DNA that includes nucleotides derived from a plant miRNA; (i) DNA that includes nucleotides of a siRNA; any of these gene suppression elements, whether transcribing to a single double-stranded RNA or to multiple double-stranded RNAs, can be designed to suppress at least one target gene, including, for example, more than one allele of a target gene, multiple target genes (or multiple segments of at least one target gene) from a single species, or target genes from different species.

As used herein a "plant" includes whole plant, transgenic plant, meristem, shoot organ/structure (for example, leaf, stem and tuber), root, flower and floral organ/structure (for example, bract, sepal, petal, stamen, carpel, anther and ovule), seed (including embryo, endosperm, and seed coat) and fruit (the mature ovary), plant tissue (for example, vascular tissue, ground tissue, and the like) and cell (for example, guard cell, egg cell, pollen, mesophyll cell, and the like), and progeny of same. The classes of plants that can be used in the disclosed methods are generally as broad as the classes of higher and lower plants amenable to transformation and breeding techniques, including angiosperms (monocotyledonous and dicotyledonous plants), gymnosperms, ferns, horsetails, psilophytes, lycophytes, bryophytes, and algae.

As used herein, a "transgenic plant" refers to a plant whose genome has been altered by the stable integration of recombinant DNA. A transgenic plant includes a plant regenerated from an originally-transformed plant cell and progeny transgenic plants from later generations or crosses of a transgenic plant.

As used herein, a "control plant" refers to a plant that does not contain the recombinant DNA that imparts an enhanced trait. A control plant is used to identify and select a transgenic plant that has an enhanced trait. A suitable control plant can be a non-transgenic plant of the parental line used to generate a transgenic plant, for example, a wild type plant devoid of a recombinant DNA. A suitable control plant can also be a transgenic plant that contains the recombinant DNA that imparts other traits, for example, a transgenic plant having enhanced herbicide tolerance. A suitable control plant can in some cases be a progeny of a hemizygous transgenic plant line that does not contain the recombinant DNA, known as a negative segregant, or a negative isoline.

As used herein, a "transgenic plant cell" refers to a plant cell that is transformed with stably-integrated, recombinant DNA, for example, by *Agrobacterium*-mediated transformation or by bombardment using microparticles coated with recombinant DNA or by other means. A plant cell of this disclosure can be an originally-transformed plant cell that exists as a microorganism or as a progeny plant cell that is regenerated into differentiated tissue, for example, into a transgenic plant with stably-integrated, recombinant DNA, or seed or pollen derived from a progeny transgenic plant.

As used herein, a "propagule" includes all products of meiosis and mitosis, including but not limited to, plant, seed and part of a plant able to propagate a new plant. Propagules include whole plants, cells, pollen, ovules, flowers, embryos, leaves, roots, stems, shoots, meristems, grains or seeds, or any plant part that is capable of growing into an entire plant. Propagule also includes graft where one portion of a plant is grafted to another portion of a different plant (even one of a different species) to create a living organism. Propagule also includes all plants and seeds produced by cloning or by bringing together meiotic products, or allowing meiotic products to come together to form an embryo or a fertilized egg (naturally or with human intervention).

As used herein, a "progeny" includes any plant, seed, plant cell, and/or regenerable plant part comprising a recombinant DNA of the present disclosure derived from an ancestor plant. A progeny can be homozygous or heterozygous for the transgene. Progeny can be grown from seeds produced by a transgenic plant comprising a recombinant DNA of the present disclosure, and/or from seeds produced by a plant fertilized with pollen or ovule from a transgenic plant comprising a recombinant DNA of the present disclosure.

As used herein, a "trait" is a physiological, morphological, biochemical, or physical characteristic of a plant or particular plant material or cell. In some instances, this characteristic is visible to the human eye, such as seed or plant size, or can be measured by biochemical techniques, such as detecting the protein, starch, certain metabolites, or oil content of seed or leaves, or by observation of a metabolic or physiological process, for example, by measuring tolerance to water deprivation or particular salt or sugar concentrations, or by the measurement of the expression level of a gene or genes, for example, by employing Northern analysis, RT-PCR, microarray gene expression assays, or reporter gene expression systems, or by agricultural observations such as hyperosmotic stress tolerance or yield. Any technique can be used to measure the amount of, comparative level of, or difference in any selected chemical compound or macromolecule in the transgenic plants.

As used herein, an "enhanced trait" means a characteristic of a transgenic plant as a result of stable integration and expression of a recombinant DNA in the transgenic plant. Such traits include, but are not limited to, an enhanced agronomic trait characterized by enhanced plant morphology, physiology, growth and development, yield, nutritional enhancement, disease or pest resistance, or environmental or chemical tolerance. An enhanced trait can also be increased drought tolerance, increased water use efficiency, cold tolerance, increased nitrogen use efficiency, increased yield, and altered phenotypes as shown in Tables 4-6 (corn, altered phenotypes), Tables 7-12 (corn), Table 13 (soybean) and Table 14 (canola). In another aspect, the trait is increased yield under non-stress conditions or increased yield under environmental stress conditions. Stress conditions can include, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, plant biomass, pod or silique number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), ear number, seed number per ear, seed size, seed weight, composition of seed (starch, oil, protein) and characteristics of seed fill.

Also used herein, the term "trait modification" encompasses altering the naturally occurring trait by producing a detectable difference in a characteristic in a plant comprising a recombinant DNA of the present disclosure relative to a plant not comprising the recombinant DNA, such as a wild-type plant, or a negative segregant. In some cases, the trait modification can be evaluated quantitatively. For example, the trait modification can entail an increase or decrease, in an observed trait as compared to a control plant. It is known that there can be natural variations in the modified trait. Therefore, the trait modification observed entails a change of the normal distribution and magnitude of the trait in the plants as compared to a control plant.

Increased yield of a plant of the present disclosure can be measured in a number of ways, including test weight, seed number per plant, seed weight, seed number per unit area (for example, seeds, or weight of seeds, per acre), bushels per acre, tons per acre, or kilo per hectare. For example, corn yield can be measured as production of shelled corn kernels per unit of production area, for example in bushels per acre or metric tons per hectare. Increased yield can result from improved utilization of key biochemical compounds, such as nitrogen, phosphorous and carbohydrate, or from improved responses to environmental stresses, such as cold, heat, drought, salt, shade, high plant density, and attack by pests or pathogens. This disclosure can also be used to provide plants with improved growth and development, and ultimately increased yield, as the result of modified expression of plant growth regulators or modification of cell cycle or photosynthesis pathways. Also of interest is the generation of plants that demonstrate increased yield with respect to a seed component that may or may not correspond to an increase in overall plant yield.

In an embodiment, the present disclosure relates to a plant with improved economically important characteristics, more specifically increased yield. More specifically the present disclosure relates to a plant comprising a polynucleotide of this disclosure that encodes a polypeptide, wherein the plant has increased yield as compared to a control plant. Many plants of this disclosure exhibited increased yield as compared to a control plant. In an embodiment, a plant of the present disclosure exhibited an improved trait that is a component of yield.

Yield can be defined as the measurable produce of economic value from a crop. Yield can be defined in the scope of quantity and/or quality. Yield can be directly dependent on several factors, for example, the number and size of organs, plant architecture (such as the number of branches, plant biomass, etc.), seed production and more. Root development, photosynthetic efficiency, nutrient uptake, stress tolerance, early vigor, delayed senescence and functional stay green phenotypes can be important factors in determining yield. Optimizing the above mentioned factors can therefore contribute to increasing crop yield.

Reference herein to an increase in yield-related traits can also be taken to refer to an increase in biomass (weight) of one or more parts of a plant, which can include above ground and/or below ground (harvestable) plant parts. In particular, such harvestable parts are seeds, and performance of the methods of the disclosure results in plants with increased yield and in particular increased seed yield relative to the seed yield of suitable control plants. The term "yield" of a plant can relate to vegetative biomass (root and/or shoot biomass), to reproductive biomass (such as corn ear biomass (unit) or corn ear biomass per plot (unit), and/or to propagules (such as seeds) of that plant.

In an embodiment, "alfalfa yield" can be measured in forage yield, the amount of above ground biomass at harvest. Factors contributing to increased biomass include increased vegetative growth, branches, nodes and internodes, leaf area, and leaf area index.

In another embodiment, "canola yield" can also be measured in silique number, number of siliques per plant, number of siliques per node, number of internodes, incidence of silique shatter, seeds per silique, seed weight per silique, improved seed, oil, or protein composition.

Additionally, "corn or maize yield" can also be measured as production of shelled corn kernels per unit of production area, ears per acre, number of kernel rows per ear, kernels per ear, weight per kernel, ear number, ear biomass and ear biomass per plot.

In yet another embodiment, "cotton yield" can be measured as bolls per plant, size of bolls, fiber quality, seed cotton yield in grams (g)/plant, seed cotton yield in pounds (lbs)/acre, lint yield in lb/acre, and number of bales.

Specific embodiment for "rice yield" can also include panicles per hill, grain per hill, and filled grains per panicle.

Still further embodiment for "soybean yield" can also include pods per plant, pods per acre, seeds per plant, seeds per pod, weight per seed, weight per pod, pods per node, number of nodes, and the number of internodes per plant.

In still further embodiment, "sugarcane yield" can be measured as cane yield (tons per acre; kilograms (kg)/hectare), total recoverable sugar (pounds per ton), and sugar yield (tons/acre).

In yet still further embodiment, "wheat yield" can include: cereal per unit area, grain number, grain weight, grain size, grains per head, seeds per head, seeds per plant, heads per acre, number of viable tillers per plant, composition of seed (for example, carbohydrates, starch, oil, and protein) and characteristics of seed fill.

The terms "yield", "seed yield" are defined above for a number of core crops. The terms "increased", "improved", "enhanced" are interchangeable and are defined herein.

In another embodiment, the present disclosure also provides a method for the production of plants having increased yield. Performance of the method gives plants increased yield. "Increased yield" can manifest as one or more of the following: (i) increased plant biomass (weight) of one or more parts of a plant, particularly aboveground (harvestable) parts, of a plant, increased root biomass (increased number of roots, increased root thickness, increased root length) or increased biomass of any other harvestable part; (ii) increased early vigor, defined herein as an improved seedling aboveground area approximately three weeks post-germination. "Early vigor" refers to active healthy plant growth especially during early stages of plant growth, and can result from increased plant fitness due to, for example, the plants being better adapted to their environment (for example, optimizing the use of energy resources, uptake of nutrients and partitioning carbon allocation between shoot and root). Early vigor in corn, for example, is a combination of the ability of corn seeds to germinate and emerge after planting and the ability of the young corn plants to grow and develop after emergence. Plants having early vigor also show increased seedling survival and better establishment of the crop, which often results in highly uniform fields with the majority of the plants reaching the various stages of development at substantially the same time, which often results in increased yield. Therefore early vigor can be determined by measuring various factors, such as kernel weight, percentage germination, percentage emergence, seedling growth, seedling height, root length, root and shoot biomass, canopy size and color and others; (iii) increased total seed yield, which includes an increase in seed biomass (seed weight) and which can be an increase in the seed weight per plant or on an individual seed basis; increased number of panicles per plant; increased pods, increased number of nodes, increased number of flowers ("florets") per panicle/plant; increased seed fill rate; increased number of filled seeds; increased seed size (length, width, area, perimeter), which can also influence the composition of seeds; increased seed volume, which can also influence the composition of seeds. Increased yield can also result in modified architecture, or can occur because of modified plant architecture; (iv) increased harvest index, which is expressed as a ratio of the yield of harvestable parts, such as seeds, over the total biomass; (v) increased kernel weight, which is extrapolated from the number of filled seeds counted and their total weight. An increased kernel weight can result from an increased seed size and/or seed weight, an increase in embryo size, endosperm size, aleurone and/or scutellum, or other parts of the seed; and vi) increased ear biomass, which is the weight of the ear and can be represented on a per ear, per plant or per plot basis.

In one embodiment, increased yield can be increased seed yield, and is selected from one of the following: (i) increased seed weight; (ii) increased number of filled seeds; and (iii) increased harvest index.

The disclosure also extends to harvestable parts of a plant such as, but not limited to seeds, leaves, fruits, flowers, bolls, stems, rhizomes, tubers and bulbs. The disclosure furthermore relates to products derived from a harvestable part of such a plant, such as dry pellets, powders, oil, fat and fatty acids, starch or proteins.

The present disclosure provides a method for increasing "yield" of a plant or "broad acre yield" of a plant or plant part defined as the harvestable plant parts per unit area, for example seeds, or weight of seeds, per acre, pounds per acre, bushels per acre, tones per acre, tons per acre, kilo per hectare.

This disclosure further provides a method of increasing yield in a plant by crossing a plant comprising a recombinant DNA molecule of the present disclosure with itself, a second plant from the same plant line, a wild type plant, or a plant from a different line of plants to produce a seed. The seed of the resultant plant can be harvested from fertile plants and be used to grow progeny generations of plant(s) of this disclosure. In addition to direct transformation of a plant with a recombinant DNA, transgenic plants can be prepared by crossing a first plant having a recombinant DNA with a second plant lacking the DNA. For example, recombinant DNA can be introduced into a first plant line that is amenable to transformation to produce a transgenic plant which can be crossed with a second plant line to introgress the recombinant DNA into the second plant line. A transgenic plant with a recombinant DNA having the polynucleotide of this disclosure provides at least one enhanced trait of increased yield, increased nitrogen use efficiency or increased water use efficiency compared to a control plant. Genetic markers associated with recombinant DNA can be used to identify transgenic progeny that is homozygous for the desired recombinant DNA. Progeny plants carrying the recombinant DNA can be back crossed into a parent line or other transgenic line multiple times, for example usually 6 to 8 generations, to produce a progeny plant with substantially the same genotype as the original transgenic parental line. The term "progeny" denotes the offspring of any generation of a parent plant prepared by the methods of this disclosure comprising the recombinant polynucleotides as described herein.

As used herein, "nitrogen use efficiency" refers to the processes which lead to an increase in the plant's yield, biomass, vigor, and growth rate per nitrogen unit applied. The processes can include the uptake, assimilation, accumulation, signaling, sensing, retranslocation (within the plant) and use of nitrogen by the plant.

As used herein, "nitrogen limiting conditions" refers to growth conditions or environments that provide less than optimal amounts of nitrogen needed for adequate or successful plant metabolism, growth, reproductive success and/or viability.

As used herein, "increased nitrogen stress tolerance" refers to the ability of plants to grow, develop, or yield normally, or grow, develop, or yield faster or better when subjected to less than optimal amounts of available/applied nitrogen, or under nitrogen limiting conditions.

As used herein, "increased nitrogen use efficiency" refers to the ability of plants to grow, develop, or yield faster or better than normal when subjected to the same amount of available/applied nitrogen as under normal or standard conditions; ability of plants to grow, develop, or yield normally, or grow, develop, or yield faster or better when subjected to less than optimal amounts of available/applied nitrogen, or under nitrogen limiting conditions.

Increased plant nitrogen use efficiency can be translated in the field into either harvesting similar quantities of yield, while supplying less nitrogen, or increased yield gained by supplying optimal/sufficient amounts of nitrogen. The increased nitrogen use efficiency can improve plant nitrogen stress tolerance, and can also improve crop quality and biochemical constituents of the seed such as protein yield and oil yield. The terms "increased nitrogen use efficiency", "enhanced nitrogen use efficiency", and "nitrogen stress tolerance" are used inter-changeably in the present disclosure to refer to plants with improved productivity under nitrogen limiting conditions.

As used herein, "water use efficiency" refers to the amount of carbon dioxide assimilated by leaves per unit of water vapor transpired. "Drought tolerance" refers to the degree to which a plant is adapted to arid or drought conditions. The physiological responses of plants to a deficit of water include leaf wilting, a reduction in leaf area, leaf abscission, and the stimulation of root growth by directing nutrients to the underground parts of the plants. Plants are more susceptible to drought during flowering and seed development (the reproductive stages), as plant's resources are deviated to support root growth. In addition, abscisic acid (ABA), a plant stress hormone, induces the closure of leaf stomata (microscopic pores involved in gas exchange), thereby reducing water loss through transpiration, and decreasing the rate of photosynthesis. These responses improve the water-use efficiency of the plant on the short term. The terms "increased water use efficiency", "enhanced water use efficiency", and "increased drought tolerance" are used inter-changeably in the present disclosure to refer to plants with improved productivity under water-limiting conditions.

As used herein, "increased water use efficiency" refers to the ability of plants to grow, develop, or yield faster or better than normal when subjected to the same amount of available/applied water as under normal or standard conditions; ability of plants to grow, develop, or yield normally, or grow, develop, or yield faster or better when subjected to reduced amounts of available/applied water (water input) or under conditions of water stress or water deficit stress.

As used herein, "increased drought tolerance" refers to the ability of plants to grow, develop, or yield normally, or grow, develop, or yield faster or better than normal when subjected to reduced amounts of available/applied water and/or under conditions of acute or chronic drought.

As used herein, "drought stress" refers to a period of dryness (acute or chronic/prolonged) that results in water deficit and subjects plants to stress and/or damage to plant tissues and/or negatively affects grain/crop yield; a period of dryness (acute or chronic/prolonged) that results in water deficit and/or higher temperatures and subjects plants to stress and/or damage to plant tissues and/or negatively affects grain/crop yield.

As used herein, "water deficit" refers to the conditions or environments that provide less than optimal amounts of water needed for adequate/successful growth and development of plants.

As used herein, "water stress" refers to the conditions or environments that provide improper (either less/insufficient or more/excessive) amounts of water than that needed for adequate/successful growth and development of plants/crops thereby subjecting the plants to stress and/or damage to plant tissues and/or negatively affecting grain/crop yield.

As used herein, "water deficit stress" refers to the conditions or environments that provide less/insufficient amounts of water than that needed for adequate/successful growth and development of plants/crops thereby subjecting the plants to stress and/or damage to plant tissues and/or negatively affecting grain yield.

As used herein, a "polynucleotide" is a nucleic acid molecule comprising a plurality of polymerized nucleotides. A polynucleotide may be referred to as a nucleic acid, oligonucleotide, nucleotide, or any fragment thereof. In many instances, a polynucleotide encodes a polypeptide (or protein) or a domain or fragment thereof.

Additionally, a polynucleotide can comprise a promoter, an intron, an enhancer region, a polyadenylation site, a translation initiation site, 5' or 3' untranslated regions, a reporter gene, a selectable marker, a scorable marker, or the like. A polynucleotide can be single-stranded or double-stranded DNA or RNA. A polynucleotide can also comprise modified bases or a modified backbone. A polynucleotide can be, for example, genomic DNA or RNA, a transcript (such as an mRNA), a cDNA, a PCR product, a cloned DNA, a synthetic DNA or RNA, or the like. A polynucleotide can be combined with carbohydrate(s), lipid(s), protein(s), or other materials to perform a particular activity such as transformation or form a composition such as a peptide nucleic acid (PNA). A polynucleotide can comprise a sequence in either sense or antisense orientations. "Oligonucleotide" is substantially equivalent to the terms amplimer, primer, oligomer, element, target, and probe and is typically single-stranded.

As used herein, a "recombinant polynucleotide" or "recombinant DNA" is a polynucleotide that is not in its native state, for example, a polynucleotide comprises a series of nucleotides (represented as a nucleotide sequence) not found in nature, or a polynucleotide is in a context other than that in which it is naturally found; for example, separated from polynucleotides with which it typically is in proximity in nature, or adjacent (or contiguous with) polynucleotides with which it typically is not in proximity. The "recombinant polynucleotide" or "recombinant DNA" refers to polynucleotide or DNA which has been genetically engineered and constructed outside of a cell including DNA containing naturally occurring DNA or cDNA or synthetic DNA. For example, the polynucleotide at issue can be cloned into a vector, or otherwise recombined with one or more additional nucleic acids.

As used herein, a "polypeptide" comprises a plurality of consecutive polymerized amino acid residues for example, at least about 15 consecutive polymerized amino acid residues. In many instances, a polypeptide comprises a series of polymerized amino acid residues that is a transcriptional regulator or a domain or portion or fragment thereof. Additionally, the polypeptide can comprise: (i) a localization domain; (ii) an activation domain; (iii) a repression domain; (iv) an oligomerization domain; (v) a protein-protein interaction domain; (vi) a DNA-binding domain; or the like. The polypeptide optionally comprises modified amino acid residues, naturally occurring amino acid residues not encoded by a codon, non-naturally occurring amino acid residues.

As used herein, "protein" refers to a series of amino acids, oligopeptide, peptide, polypeptide or portions thereof whether naturally occurring or synthetic.

As used herein a "recombinant polypeptide" is a polypeptide produced by translation of a recombinant polynucleotide.

A "synthetic polypeptide" is a polypeptide created by consecutive polymerization of isolated amino acid residues using methods well known in the art.

Recombinant DNA constructs are assembled using methods known to persons of ordinary skill in the art and typically comprise a promoter operably linked to DNA, the expression of which provides an enhanced agronomic trait. Other construct components can include additional regulatory elements, such as 5' leaders and introns for enhancing transcription, 3' untranslated regions (such as polyadenylation signals and sites), and DNA for transit or targeting or signal peptides. A "DNA construct" as used in the present disclosure comprises at least one expression cassette having a promoter operable in plant cells and a polynucleotide of the present disclosure encoding a protein or variant of a protein or fragment of a protein that is functionally defined to maintain activity in host cells including plant cells, plant parts, explants and plants. DNA constructs are made that contain various genetic elements necessary for the expression of noncoding and coding polynucleotides in plants. Promoters, leaders, enhancers, introns, transit or targeting or signal peptide sequences, 3' transcriptional termination regions are genetic elements that can be operably linked in a DNA construct.

Percent identity describes the extent to which polynucleotides or protein segments are invariant in an alignment of sequences, for example, nucleotide sequences or amino acid sequences. An alignment of sequences is created by manually aligning two sequences, for example, a stated sequence, as provided herein, as a reference, and another sequence, to produce the highest number of matching elements, for example, individual nucleotides or amino acids, while allowing for the introduction of gaps into either sequence. An "identity fraction" for a sequence aligned with a reference sequence is the number of matching elements, divided by the full length of the reference sequence, not including gaps introduced by the alignment process into the reference sequence. "Percent identity" ("% identity") as used herein is the identity fraction times 100.

As used herein, a "functional fragment" refers to a portion of a polypeptide provided herein which retains full or partial molecular, physiological or biochemical function of the full length polypeptide. A functional fragment often contains the domain(s), such as Pfam domains, identified in the polypeptide provided in the

SEQUENCE LISTING

As used herein, a "homolog" or "homologues" means a protein in a group of proteins that perform the same biological function, for example, proteins that belong to the same Pfam protein family and that provide a common enhanced trait in transgenic plants of this disclosure. Homologs are expressed by homologous genes. With reference to homologous genes, homologs include orthologs, for example, genes expressed in different species that evolved from a common ancestral genes by speciation and encode proteins retain the same function, but do not include paralogs, for example, genes that are related by duplication but have evolved to encode proteins with different functions. Homologous genes include naturally occurring alleles and artificially-created variants. Degeneracy of the genetic code provides the possibility to substitute at least one base of the protein encoding sequence of a gene with a different base without causing the amino acid sequence of the polypeptide produced from the gene to be changed. When optimally aligned, homolog proteins, or their respective nucleotides, have typically at least about 60% identity, in some instances at least about 70%, at least about 75%, at least about 80%, at least about 85%, at least about 90%, at least about 92%, at least about 94%, at least about 95%, at least about 96%, at least about 97%, at least about 98%, at least about 99%, and even at least about 99.5% identity over the full length of a protein identified as being associated with imparting an enhanced trait when expressed in plant cells. In one aspect of the disclosure homolog proteins have amino acid sequences or corresponding nucleotide sequences that have at least about 80%, at least about 85%, at least about 90%, at least about 92%, at least about 94%, at least about 95%, at least about 96%, at least about 97%, at least about 98%, at least about 99%, and at least about 99.5% identity to a consensus amino acid sequence of proteins and homologs that can be built from sequences disclosed herein.

Homologs are inferred from sequence similarity, by comparison of protein sequences, for example, manually or by use of a computer-based tool using well-known sequence comparison algorithms such as BLAST and FASTA. A sequence search and local alignment program, for example, BLAST, can be used to search query protein sequences of a base organism against a database of protein sequences of various organisms, to find similar sequences, and the summary Expectation value (E-value) can be used to measure the level of sequence similarity. Because a protein hit with the lowest E-value for a particular organism may not necessarily be an ortholog or be the only ortholog, a reciprocal query is used to filter hit sequences with significant E-values for ortholog identification. The reciprocal query entails search of the significant hits against a database of protein sequences of the base organism. A hit can be identified as an ortholog, when the reciprocal query's best hit is the query protein itself or a paralog of the query protein. With the reciprocal query process orthologs are further differentiated from paralogs among all the homologs, which allows for the inference of functional equivalence of genes. A further aspect of the homologs encoded by DNA useful in the transgenic plants of the invention are those proteins that differ from a disclosed protein as the result of deletion or insertion of one or more amino acids in a native sequence.

Other functional homolog proteins differ in one or more amino acids from those of a trait-improving protein disclosed herein as the result of one or more of the well-known conservative amino acid substitutions, for example, valine is a conservative substitute for alanine and threonine is a conservative substitute for serine. Conservative substitutions for an amino acid within the native sequence can be selected from other members of a class to which the naturally occurring amino acid belongs. Representative amino acids within these various classes include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, tyrosine, asparagine, and glutamine; and (4) neutral nonpolar (hydrophobic) amino acids such as alanine, leucine, isoleucine, valine, proline, phenylalanine, tryptophan, and methionine. Conserved substitutes for an amino acid within a native protein or polypeptide can be selected from other members of the group to which the naturally occurring amino acid belongs. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side 30 chains is cysteine and methionine. Naturally conservative amino acids substitution groups are: valine-leucine, valine-isoleucine, phenylalanine-tyrosine, lysine-arginine, alaninevaline, aspartic acid-glutamic acid, and asparagine-glutamine. A further aspect of the disclosure includes proteins that differ in one or more amino acids from those of a described protein sequence as the result of deletion or insertion of one or more amino acids in a native sequence.

Homologs can be identified for the polypeptide sequences provided in Table 1, using the reciprocal search process as described above. The NCBI "blastp" program can be used for the sequence search, with E-value cutoff of Ie-4 to identify the initial significant hits. NCBI non-redundant amino-acid dataset can be used as the database of protein sequences of various organisms. Homologs with at least 95% identity over 95% of the length of the polypeptide sequences provided in Table 1 would be kept. From the sequences of the proteins identified in SEQ ID NOs: 6, 8, 12, and 16, the corresponding homologous protein sequences set forth as SEQ ID NOs: 23 (homolog of SEQ ID NO: 6), 24 (homolog of SEQ ID NO: 8), SEQ ID NOs: 25 and 26 (homologs of SEQ ID NO: 12), SEQ ID NO: 27 (homolog of SEQ ID NO: 14), and SEQ ID NOs: 28 and 29 (homologs of SEQ ID NO: 16) were identified for preparing additional transgenic seeds and plants with enhanced agronomic traits.

In general, the term "variant" refers to molecules with some differences, generated synthetically or naturally, in their nucleotide or amino acid sequences as compared to a reference (native) polynucleotides or polypeptides, respectively. These differences include substitutions, insertions, deletions or any desired combinations of such changes in a native polynucleotide or amino acid sequence.

With regard to polynucleotide variants, differences between presently disclosed polynucleotides and polynucleotide variants are limited so that the nucleotide sequences of the former and the latter are similar overall and, in many regions, identical. Due to the degeneracy of the genetic code, differences between the former and the latter nucleotide sequences can be silent (for example, the amino acids encoded by the polynucleotide are the same, and the variant polynucleotide sequence encodes the same amino acid sequence as the presently disclosed polynucleotide). Variant nucleotide sequences can encode different amino acid sequences, in which case such nucleotide differences will result in amino acid substitutions, additions, deletions, insertions, truncations or fusions with respect to the similarly disclosed polynucleotide sequences. These variations can result in polynucleotide variants encoding polypeptides that share at least one functional characteristic. The degeneracy of the genetic code also dictates that many different variant polynucleotides can encode identical and/or substantially similar polypeptides.

As used herein "gene" or "gene sequence" refers to the partial or complete coding sequence of a gene, its complement, and its 5' and/or 3' untranslated regions. A gene is also a functional unit of inheritance, and in physical terms is a particular segment or sequence of nucleotides along a molecule of DNA (or RNA, in the case of RNA viruses) involved in producing a polypeptide chain. The latter can be subjected to subsequent processing such as chemical modification or folding to obtain a functional protein or polypeptide. By way of example, a transcriptional regulator gene encodes a transcriptional regulator polypeptide, which can be functional or require processing to function as an initiator of transcription.

As used herein, the term "promoter" refers generally to a DNA molecule that is involved in recognition and binding of RNA polymerase II and other proteins (trans-acting transcription factors) to initiate transcription. A promoter can be initially isolated from the 5' untranslated region (5' UTR) of a genomic copy of a gene. Alternately, promoters can be synthetically produced or manipulated DNA molecules. Promoters can also be chimeric, that is a promoter produced through the fusion of two or more heterologous DNA molecules. Plant promoters include promoter DNA obtained from plants, plant viruses, fungi and bacteria such as *Agrobacterium* and *Bradyrhizobium* bacteria.

Promoters which initiate transcription in all or most tissues of the plant are referred to as "constitutive" promoters. Promoters which initiate transcription during certain periods or stages of development are referred to as "developmental" promoters. Promoters whose expression is enhanced in certain tissues of the plant relative to other plant tissues are referred to as "tissue enhanced" or "tissue preferred" promoters. Promoters which express within a specific tissue of the plant, with little or no expression in other plant tissues are referred to as "tissue specific" promoters. A promoter that expresses in a certain cell type of the plant, for example a microspore mother cell, is referred to as a "cell type specific" promoter. An "inducible" promoter is a promoter in which transcription is initiated in response to an environmental stimulus such as cold, drought or light; or other stimuli such as wounding or chemical application. Many physiological and biochemical processes in plants exhibit endogenous rhythms with a period of about 24 hours. A "diurnal promoter" is a promoter which exhibits altered expression profiles under the control of a circadian oscillator. Diurnal regulation is subject to environmental inputs such as light and temperature and coordination by the circadian clock.

As used herein, the term "leader" refers to a DNA molecule isolated from the untranslated 5' region (5' UTR) of a genomic copy of a gene and is defined generally as a nucleotide segment between the transcription start site (TSS) and the protein coding sequence start site. Alternately, leaders can be synthetically produced or manipulated DNA elements. A leader can be used as a 5' regulatory element for modulating expression of an operably linked transcribable polynucleotide molecule.

As used herein, the term "intron" refers to a DNA molecule that can be isolated or identified from the genomic copy of a gene and can be defined generally as a region spliced out during mRNA processing prior to translation.

Alternately, an intron can be a synthetically produced or manipulated DNA element. An intron can contain enhancer elements that effect the transcription of operably linked genes. An intron can be used as a regulatory element for modulating expression of an operably linked transcribable polynucleotide molecule. A DNA construct can comprise an intron, and the intron may or may not be heterologous with respect to the transcribable polynucleotide molecule.

As used herein, the term "enhancer" or "enhancer element" refers to a cis-acting transcriptional regulatory element, a.k.a. cis-element, which confers an aspect of the overall expression pattern, but is usually insufficient alone to drive transcription, of an operably linked polynucleotide. Unlike promoters, enhancer elements do not usually include a transcription start site (TSS) or TATA box or equivalent sequence. A promoter can naturally comprise one or more enhancer elements that affect the transcription of an operably linked polynucleotide. An isolated enhancer element can also be fused to a promoter to produce a chimeric promoter cis-element, which confers an aspect of the overall modulation of gene expression. A promoter or promoter fragment can comprise one or more enhancer elements that effect the transcription of operably linked genes. Many promoter enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element can function to bind transcription factors that regulate transcription. Some enhancer elements bind more than one transcription factor, and transcription factors can interact with different affinities with more than one enhancer domain.

Expression cassettes of this disclosure can include a "transit peptide" or "targeting peptide" or "signal peptide" molecule located either 5' or 3' to or within the gene(s). These terms generally refer to peptide molecules that when linked to a protein of interest directs the protein to a particular tissue, cell, subcellular location, or cell organelle. Examples include, but are not limited to, chloroplast transit peptides (CTPs), chloroplast targeting peptides, mitochondrial targeting peptides, nuclear targeting signals, nuclear exporting signals, vacuolar targeting peptides, vacuolar sorting peptides. For description of the use of chloroplast transit peptides see U.S. Pat. Nos. 5,188,642 and 5,728,925. For description of the transit peptide region of an *Arabidopsis* EPSPS gene see Klee, H. J. et al (*MGG* (1987) 210:437-442. Expression cassettes of this disclosure can also include an intron or introns. Expression cassettes of this disclosure can contain a DNA near the 3' end of the cassette that acts as a signal to terminate transcription from a heterologous nucleic acid and that directs polyadenylation of the resultant mRNA. These are commonly referred to as "3'-untranslated regions" or "3'-non-coding sequences" or "3'-UTRs". The "3' non-translated sequences" means DNA sequences located downstream of a structural nucleotide sequence and include sequences encoding polyadenylation and other regulatory signals capable of affecting mRNA processing or gene expression. The polyadenylation signal functions in plants to cause the addition of polyadenylate nucleotides to the 3' end of the mRNA precursor. The polyadenylation signal can be derived from a natural gene, from a variety of plant genes, or from T-DNA. An example of a polyadenylation sequence is the nopaline synthase 3' sequence (nos 3'; Fraley et al., *Proc. Natl. Acad. Sci. USA* 80: 4803-4807, 1983). The use of different 3' non-translated sequences is exemplified by Ingelbrecht et al., *Plant Cell* 1:671-680, 1989. Recombinant DNA constructs in this disclosure generally include a 3' element that typically contains a polyadenylation signal and site. Well-known 3' elements include those from *Agrobacterium tumefaciens* genes such as nos 3', tml 3', tmr 3', tms 3', ocs 3', tr7 3', for example disclosed in U.S. Pat. No. 6,090,627; 3' elements from plant genes such as wheat (*Triticum aesevitum*) heat shock protein 17 (Hsp 17 3 '), a wheat ubiquitin gene, a wheat fructose-1,6-biphosphatase gene, a rice glutelin gene, a rice lactate dehydrogenase gene and a rice beta-tubulin gene, all of which are disclosed in US Patent Application Publication No. US 2002/0192813 A1; and the pea (*Pisum sativum*) ribulose biphosphate carboxylase gene (rbs 3), and 3' elements from the genes within the host plant.

Expression cassettes of this disclosure can also contain one or more genes that encode selectable markers and confer resistance to a selective agent such as an antibiotic or a herbicide. A number of selectable marker genes are known in the art and can be used in the present disclosure: selectable marker genes conferring tolerance to antibiotics like kanamycin and paromomycin (nptII), hygromycin B (aph IV), spectinomycin (aadA), US Patent Publication No. US 2009/0138985 A1 and gentamycin (aac3 and aacC4) or tolerance to herbicides like glyphosate (for example, 5-enolpyruvylshikimate-3-phosphate synthase (EPSPS), U.S. Pat. Nos. 5,627,061; 5,633,435; 6,040,497; 5,094,945), sulfonyl herbicides (for example, acetohydroxyacid synthase or acetolactate synthase conferring tolerance to acetolactate synthase inhibitors such as sulfonylurea, imidazolinone, triazolopyrimidine, pyrimidyloxybenzoates and phthalide (US Patents Nos. U.S. Pat. Nos. 6,225,105; 5,767,366; 4,761,373; 5,633,437; 6,613,963; 5,013,659; 5,141,870; 5,378,824; and 5,605,011)), bialaphos or phosphinothricin or derivatives (for example, phosphinothricin acetyltransferase (bar) tolerance to phosphinothricin or glufosinate (US Patents Nos. U.S. Pat. Nos. 5,646,024; 5,561,236; 5,276,268; 5,637,489; 5,273,894); dicamba (dicamba monooxygenase, US Patent Application Publications No. US 2003/0115626 A1), or sethoxydim (modified acetyl-coenzyme A carboxylase for conferring tolerance to cyclohexanedione (sethoxydim)), and aryloxyphenoxypropionate (haloxyfop, U.S. Pat. No. 6,414,222).

Transformation vectors of this disclosure can contain one or more "expression cassettes", each comprising a native or non-native plant promoter operably linked to a polynucleotide sequence of interest, which is operably linked to a 3' UTR termination signal, for expression in an appropriate host cell. It also typically comprises sequences required for proper translation of the polynucleotide or transgene. As used herein, the term "transgene" refers to a polynucleotide molecule artificially incorporated into a host cell's genome. Such a transgene can be heterologous to the host cell. The expression cassette comprising the nucleotide sequence of interest can be chimeric, meaning that at least one of its components is heterologous with respect to at least one of its other components. As used herein the term "chimeric" refers to a DNA molecule that is created from two or more genetically diverse sources, for example, a first molecule from one gene or organism and a second molecule from another gene or organism.

As used herein "operably linked" means the association of two or more DNA fragments in a recombinant DNA construct so that the function of one, for example, protein-encoding DNA, is controlled by the other, for example, a promoter.

As used herein "expressed" means produced, for example, the information from a gene is used in the synthesis of a functional gene product. These products are often proteins. For example, a protein is expressed in a plant cell when its cognate DNA is transcribed to mRNA that is translated to the protein. In the case of non-protein coding gene/sequence, the product is a functional RNA. An "expressed" protein can also include its truncated version (for example, N-terminal truncated, C-terminal truncated or internal truncated) as long as the truncated version maintains the same or similar functionality as the full length version.

Transgenic plants can comprise a stack of one or more polynucleotides disclosed herein resulting in the production of multiple polypeptide sequences. Transgenic plants comprising stacks of polynucleotides can be obtained by either or both of traditional breeding methods or through genetic engineering methods. These methods include, but are not limited to, crossing individual transgenic lines each comprising a polynucleotide of interest, transforming a transgenic plant comprising a first gene disclosed herein with a second gene, and co-transformation of genes into a single plant cell. Co-transformation of genes can be carried out using single transformation vectors comprising multiple genes or multiples vectors each comprising one or more genes.

Transgenic plants comprising or derived from plant cells of this disclosure transformed with recombinant DNA can be further enhanced with stacked traits, for example, a crop plant having an enhanced trait resulting from expression of DNA disclosed herein in combination with herbicide and/or pest resistance traits. For example, genes of the current disclosure can be stacked with other traits of agronomic interest, such as a trait providing herbicide resistance, or insect resistance, such as using a gene from *Bacillus thuringensis* to provide resistance against lepidopteran, coliopteran, homopteran, hemiopteran, and other insects, or improved quality traits such as improved nutritional value. Herbicides to which transgenic plant tolerance has been demonstrated and the method of the present disclosure can be applied include, but are not limited to, glyphosate, dicamba, glufosinate, sulfonylurea, bromoxynil and norflurazon herbicides. Polynucleotide molecules encoding proteins involved in herbicide tolerance are well-known in the art and include, but are not limited to, a polynucleotide molecule encoding 5-enolpyruvylshikimate-3-phosphate synthase (EPSPS) disclosed in US Patent Nos. U.S. Pat. Nos. 5,094,945; 5,627,061; 5,633,435 and 6,040,497 for imparting glyphosate tolerance; polynucleotide molecules encoding a glyphosate oxidoreductase (GOX) disclosed in U.S. Pat. No. 5,463,175 and a glyphosate-N-acetyl transferase (GAT) disclosed in US Patent Application Publication No. US 2003/0083480 A1 also for imparting glyphosate tolerance; dicamba monooxygenase disclosed in US Patent Application Publication No. US 2003/0135879 A1 for imparting dicamba tolerance; a polynucleotide molecule encoding bromoxynil nitrilase (Bxn) disclosed in U.S. Pat. No. 4,810,648 for imparting bromoxynil tolerance; a polynucleotide molecule encoding phytoene desaturase (crtI) described in Misawa et al, (1993) *Plant J.* 4:833-840 and in Misawa et al, (1994) *Plant J.* 6:481-489 for norflurazon tolerance; a polynucleotide molecule encoding acetohydroxyacid synthase (AHAS, aka ALS) described in Sathasiivan et al. (1990) *Nucl. Acids Res.* 18:2188-2193 for imparting tolerance to sulfonylurea herbicides; polynucleotide molecules known as bar genes disclosed in DeBlock, et al. (1987) *EMBO J.* 6:2513-2519 for imparting glufosinate and bialaphos tolerance as disclosed in U.S. Pat. No. 7,112,665; polynucleotide molecules disclosed in U.S. Pat. No. 6,107,549 for imparting pyridine herbicide resistance; molecules and methods for imparting tolerance to multiple herbicides such as glyphosate, atrazine, ALS inhibitors, isoxoflutole and glufosinate herbicides are disclosed in U.S. Pat. No. 6,376,754 and US Patent Application Publication No. US 2002/0112260. Molecules and methods for imparting insect/nematode/virus resistance are disclosed in US Patent Nos. U.S. Pat. Nos. 5,250,515; 5,880,275; 6,506,599; 5,986,175 and US Patent Application Publication No. US 2003/0150017 A1.

Plant Cell Transformation Methods

Numerous methods for transforming chromosomes in a plant cell with recombinant DNA are known in the art and are used in methods of producing a transgenic plant cell and plant. Two effective methods for such transformation are *Agrobacterium*-mediated transformation and microprojectile bombardment-mediated transformation. Microprojectile bombardment methods are illustrated in US Patent Nos. U.S. Pat. No. 5,015,580 (soybean); U.S. Pat. No. 5,550,318 (corn); U.S. Pat. No. 5,538,880 (corn); U.S. Pat. No. 5,914,451 (soybean); U.S. Pat. No. 6,160,208 (corn); U.S. Pat. No. 6,399,861 (corn); U.S. Pat. No. 6,153,812 (wheat) and U.S. Pat. No. 6,365,807 (rice). *Agrobacterium*-mediated transformation methods are described in US Patent Nos. U.S. Pat. No. 5,159,135 (cotton); U.S. Pat. No. 5,824,877 (soybean); U.S. Pat. No. 5,463,174 (canola); U.S. Pat. No. 5,591,616 (corn); U.S. Pat. No. 5,846,797 (cotton); U.S. Pat. No. 6,384,301 (soybean), U.S. Pat. No. 7,026,528 (wheat) and U.S. Pat. No. 6,329,571 (rice), US Patent Application Publication No. US 2004/0087030 A1 (cotton), and US Patent Application Publication No. US 2001/0042257 A1 (sugar beet), all of which are incorporated herein by reference for enabling the production of transgenic plants. Transformation of plant material is carried out in tissue culture on nutrient media, for example, a mixture of nutrients that allow cells to grow in vitro. Recipient cell targets include, but are not limited to, meristem cells, shoot tips, hypocotyls, calli, immature or mature embryos, and gametic cells such as microspores, pollen, sperm and egg cells. Callus can be initiated from tissue sources including, but not limited to, immature or mature embryos, hypocotyls, seedling apical meristems, microspores and the like. Cells containing a transgenic nucleus are grown into transgenic plants.

In addition to direct transformation of a plant material with a recombinant DNA, a transgenic plant can be prepared by crossing a first plant comprising a recombinant DNA with a second plant lacking the recombinant DNA. For example, recombinant DNA can be introduced into a first plant line that is amenable to transformation, which can be crossed with a second plant line to introgress the recombinant DNA into the second plant line. A transgenic plant with recombinant DNA providing an enhanced trait, for example, enhanced yield, can be crossed with a transgenic plant line having another recombinant DNA that confers another trait, for example herbicide resistance, pest resistance or enhanced water use efficiency to produce progeny plants having recombinant DNA that confers both traits. Typically, in such breeding for combining traits the transgenic plant donating the additional trait is the male line and the transgenic plant carrying the base traits is the female line. The progeny of this cross will segregate such that some of the plants will carry the DNA for both parental traits and some will carry DNA for one parental trait; such plants can be identified by markers associated with parental recombinant DNA, for example, marker identification by analysis for recombinant DNA or, in the case where a selectable marker is linked to the recombinant DNA, by application of a selective agent such as a herbicide for use with a herbicide tolerance marker, or by selection for the enhanced trait. Progeny plants carrying DNA for both parental traits can be crossed back into the female parent line multiple times, for example usually 6 to 8 generations, to produce a progeny plant with substantially the same genotype as the original transgenic parental line but for the recombinant DNA of the other transgenic parental line.

In transformation, DNA is typically introduced into only a small percentage of target plant cells in any one transformation experiment. Marker genes are used to provide an efficient system for identification of those cells that are stably transformed by receiving and integrating a recombinant DNA molecule into their genomes. Preferred marker genes provide selective markers which confer resistance to a selective agent, such as an antibiotic or a herbicide. Any of the herbicides to which plants of this disclosure can be resistant is a agent for selective markers. Potentially transformed cells are exposed to the selective agent. In the population of surviving cells are those cells where, generally, the resistance-conferring gene is integrated and expressed at sufficient levels to permit cell survival. Cells can be tested further to confirm stable integration of the exogenous DNA. Commonly used selective marker genes include those conferring resistance to antibiotics such as kanamycin and paromomycin (nptII), hygromycin B (aph IV), spectinomycin (aadA) and gentamycin (aac3 and aacC4) or resistance to herbicides such as glufosinate (bar or pat), dicamba (DMO) and glyphosate (aroA or EPSPS). Examples of such selectable markers are illustrated in US Patent Nos. U.S. Pat. Nos. 5,550,318; 5,633,435; 5,780,708 and 6,118,047. Markers which provide an ability to visually screen transformants can also be employed, for example, a gene expressing a colored or fluorescent protein such as a luciferase or green fluorescent protein (GFP) or a gene expressing a beta-glucuronidase or uidA gene (GUS) for which various chromogenic substrates are known.

Plant cells that survive exposure to a selective agent, or plant cells that have been scored positive in a screening assay, may be cultured in vitro to regenerate plantlets. Developing plantlets regenerated from transformed plant cells can be transferred to plant growth mix, and hardened off, for example, in an environmentally controlled chamber at about 85% relative humidity, 600 ppm $CO_2$, and 25-250 micro-einsteins $M^{-2}$ $s^{-1}$ of light, prior to transfer to a greenhouse or growth chamber for maturation. Plants are regenerated from about 6 weeks to 10 months after a transformant is identified, depending on the initial tissue, and plant species. Plants can be pollinated using conventional plant breeding methods known to those of skill in the art to produce seeds, for example self-pollination is commonly used with transgenic corn. The regenerated transformed plant or its progeny seed or plants can be tested for expression of the recombinant DNA and selected for the presence of an enhanced agronomic trait.

Transgenic Plants and Seeds

Transgenic plants derived from transgenic plant cells having a transgenic nucleus of this disclosure are grown to produce transgenic seed and haploid pollen of this disclosure. Such plants can be identified either by the presence of the transgene(s) using molecular techniques known in the art, or by selection of transformed plants or progeny seed for an enhanced trait. For efficiency a selection method is designed to evaluate multiple transgenic plants (events) comprising the recombinant DNA, for example, multiple plants from 2 to 20 or more transgenic events. Transgenic plants grown from transgenic seeds provided herein demonstrate improved agronomic traits that contribute to increased yield or other traits that provide increased plant value, including, for example, improved seed quality. Of particular interest are plants having increased water use efficiency or drought tolerance, enhanced high temperature or cold tolerance, increased yield, and increased nitrogen use efficiency.

Table 1 provides a list of protein-encoding DNA ("genes") as recombinant DNA for production of transgenic plants with enhanced traits, the elements of Table 1 are described by reference to:

"PEP SEQ ID NO" which identifies an amino acid sequence.

"NUC SEQ ID NO" which identifies a DNA sequence.

"Gene ID" which refers to an arbitrary identifier.

"Protein Name" which is a common name for protein encoded by the recombinant DNA.

TABLE 1

| NUC SEQ ID NO | PEP SEQ ID NO | Gene ID | Protein Name |
|---|---|---|---|
| 1 | 2 | TRDX2-1 | Arabidopsis basic helix-loop-helix protein |
| 3 | 4 | TRDX2-2 | Corn uridine phosphate glycosyl transferase protein |
| 5 | 6 | TRDX2-3 | Arabidopsis At3g60820 proteosome component protein |
| 7 | 8 | TRDX2-4 | Arabidopsis actin-like protein 4 |
| 9 | 10 | TRDX2-5 | Arabidopsis transcription factor S-II domain-containing protein |
| 11 | 12 | TRDX2-6 | Arabidopsis protein homologous to rice OSJNBa0064D20.11 |
| 13 | 14 | TRDX2-7 | Pyropia petJ_18146963 protein |
| 15 | 16 | TRDX2-8 | Corn A1ZM043652_s_at_Os01g0678600 protein |

Table 2 provides a list of suppression elements as recombinant DNA for production of transgenic plants with enhanced traits, the elements of Table 2 are described by reference to:

"SUP SEQ ID NO" which identifies a suppression element sequence.

"Target Gene NUC SEQ ID NO" which identifies a target gene nucleotide sequence for suppression.

"Target Gene PEP SEQ ID NO Gene ID" which identifies an amino acid sequence of a target gene "Gene ID", which refers to an identifier.

"Target Protein Name" which is a common name for protein encoded by the target gene DNA.

TABLE 2

| SUP (NUC) SEQ ID NO | Target Gene (NUC) SEQ ID NO | Target Gene (PEP) SEQ ID NO | Gene ID | Target Protein Name |
|---|---|---|---|---|
| 17 | 18 | 19 | TRDX2-9 | Corn DWARF4-like protein |
| 20 | 21 | 22 | TRDX2-10 | Corn ribozyme inactivating protein |

Selection Methods for Transgenic Plants with Enhanced Traits

Within a population of transgenic plants each regenerated from a plant cell with recombinant DNA, many plants that survive to fertile transgenic plants that produce seeds and progeny plants will not exhibit an enhanced agronomic trait. Selection from the population is necessary to identify one or more transgenic plants with an enhanced trait. Transgenic plants having enhanced traits are selected from populations of plants regenerated or derived from plant cells transformed as described herein by evaluating the plants in a variety of assays to detect an enhanced trait, for example, increased water use efficiency or drought tolerance, enhanced high temperature or cold tolerance, increased yield, increased nitrogen use efficiency, enhanced seed composition such as enhanced seed protein and enhanced seed oil. These assays can take many forms including, but not limited to, direct screening for the trait in a greenhouse or field trial or by screening for a surrogate trait. Such analyses can be directed to detecting changes in the chemical composition, biomass, physiological property, or morphology of the plant. Changes in chemical compositions such as nutritional composition of grain can be detected by analysis of the seed composition and content of protein, free amino acids, oil, free fatty acids, starch or tocopherols. Changes in chemical compositions can also be detected by analysis of contents in leaves, such as chlorophyll or carotenoid contents. Changes in biomass characteristics can be evaluated on greenhouse or field grown plants and can include plant height, stem diameter, root and shoot dry weights, canopy size; and, for corn plants, ear length, ear diameter, ear biomass and ear biomass per plot. Changes in physiological properties can be identified by evaluating responses to stress conditions, for example, assays using imposed stress conditions such as water deficit, nitrogen deficiency, cold growing conditions, pathogen or insect attack or light deficiency, or increased plant density. Changes in morphology can be measured by visual observation of tendency of a transformed plant to appear to be a normal plant as compared to changes toward bushy, taller, thicker, narrower leaves, striped leaves, knotted trait, chlorosis, albino, anthocyanin production, or altered tassels, ears or roots. Other selection properties include days to pollen shed, days to silking, leaf extension rate, chlorophyll content, leaf temperature, stand, seedling vigor, internode length, plant height, leaf number, leaf area, tillering, brace roots, stay green or delayed senescence, stalk lodging, root lodging, plant health, barreness/prolificacy, green snap, and pest resistance. In addition, phenotypic characteristics of harvested grain can be evaluated, including number of kernels per row on the ear, number of rows of kernels on the ear, kernel abortion, kernel weight, kernel size, kernel density, ear biomass, and physical grain quality.

Assays for screening for a desired trait are readily designed by those practicing in the art. The following illustrates screening assays for corn traits using hybrid corn plants. The assays can be readily adapted for screening other plants such as canola, wheat, cotton and soybean either as hybrids or inbreds.

Transgenic corn plants having increased nitrogen use efficiency can be identified by screening transgenic plants in the field under the same and sufficient amount of nitrogen supply as compared to control plants, where such plants provide higher yield as compared to control plants. Transgenic corn plants having increased nitrogen use efficiency can also be identified where such plants provide higher yield as compared to by screening transgenic plants in the field under reduced amount of nitrogen supply as control plants under the same nitrogen limiting conditions.

Transgenic corn plants having increased yield are identified by screening progenies of the transgenic plants over multiple locations for several years with plants grown under optimal production management practices and maximum weed and pest control. Selection methods can be applied in multiple and diverse geographic locations, for example up to 16 or more locations, over one or more planting seasons, for example at least two planting seasons, to statistically distinguish yield improvement from natural environmental effects.

Transgenic corn plants having increased water use efficiency or drought tolerance are identified by screening plants in an assay where water is withheld for a period to induce stress followed by watering to revive the plants. For example, a selection process imposes 3 drought/re-water cycles on plants over a total period of 15 days after an initial stress free growth period of 11 days. Each cycle consists of 5 days, with no water being applied for the first four days and a water quenching on the 5th day of the cycle. The primary phenotypes analyzed by the selection method are the changes in plant growth rate as determined by height and biomass during a vegetative drought treatment.

Transgenic cotton plants with increased yield and increased water use efficiency are identified by growing under variable water conditions. Specific conditions for cotton include growing a first set of transgenic and control plants under "wet" conditions, i.e. irrigated in the range of 85 to 100 percent of evapotranspiration to provide leaf water potential of −14 to −18 bars, and growing a second set of transgenic and control plants under "dry" conditions, for example, irrigated in the range of 40 to 60 percent of evapotranspiration to provide a leaf water potential of −21 to −25 bars. Pest control, such as weed and insect control is applied equally to both wet and dry treatments as needed. Data gathered during the trial includes weather records throughout the growing season including detailed records of rainfall; soil characterization information; any herbicide or insecticide applications; any gross agronomic differences observed such as leaf morphology, branching habit, leaf color, time to flowering, and fruiting pattern; plant height at various points during the trial; stand density; node and fruit number including node above white flower and node above crack boll measurements; and visual wilt scoring. Cotton boll samples are taken and analyzed for lint fraction and fiber quality. The cotton is harvested at the normal harvest timeframe for the trial area. Increased water use efficiency is indicated by increased yield, improved relative water content, enhanced leaf water potential, increased biomass, enhanced leaf extension rates, and improved fiber parameters.

Although the plant cells and methods of this disclosure can be applied to any plant cell, plant, seed or pollen, for example, any fruit, vegetable, grass, tree or ornamental plant, the various aspects of the disclosure are applied to corn, soybean, cotton, canola, rice, barley, oat, wheat, turf grass, alfalfa, sugar beet, sunflower, *quinoa* and sugar cane plants.

The following examples are included to demonstrate aspects of the disclosure. Those of skill in the art should, in light of the present disclosure, appreciate that many changes can be made in the specific aspects which are disclosed and still obtain a like or similar results without departing from the spirit and scope of the disclosure.

Example 1. Corn Transformation

This example illustrates transformation methods in producing a transgenic corn plant cell, plant, and seed having an enhanced trait, for example, altered phenotypes as shown in Tables 4-6 or increased water use efficiency or drought tolerance, increased yield, and increased nitrogen use efficiency as shown in Tables 7-12.

For *Agrobacterium*-mediated transformation of corn embryo cells corn plants were grown in the greenhouse and ears were harvested when the embryos were 1.5 to 2.0 mm in length. Ears were surface-sterilized by spraying or soaking the ears in 80% ethanol, followed by air drying. Immature embryos were isolated from individual kernels on surface-sterilized ears. Shortly after excision, immature maize embryos were inoculated with overnight grown *Agrobacterium* cells, and incubated at room temperature with *Agrobacterium* for 5-20 minutes. Inoculated immature embryos were then co-cultured with *Agrobacterium* for 1 to 3 days at 23° C. in the dark. Co-cultured embryos were transferred to selection media and cultured for approximately two weeks to allow embryogenic callus to develop. Embryogenic calli were transferred to culture medium containing glyphosate and subcultured at about two week intervals. Transformed plant cells were recovered 6 to 8 weeks after initiation of selection.

For *Agrobacterium*-mediated transformation of maize callus immature embryos are cultured for approximately 8-21 days after excision to allow callus to develop. Callus is then incubated for about 30 minutes at room temperature with the *Agrobacterium* suspension, followed by removal of the liquid by aspiration. The callus and *Agrobacterium* are co-cultured without selection for 3-6 days followed by selection on paromomycin for approximately 6 weeks, with biweekly transfers to fresh media. Paromomycin resistant calli are identified about 6-8 weeks after initiation of selection.

To regenerate transgenic corn plants individual transgenic calli resulting from transformation and selection were placed on media to initiate shoot and root development into plantlets. Plantlets were transferred to potting soil for initial growth in a growth chamber at 26° C. followed by a mist bench before transplanting to 5 inch pots where plants were grown to maturity. The regenerated plants were self-fertilized and seeds were harvested for use in one or more methods to select seeds, seedlings or progeny second generation transgenic plants (R2 plants) or hybrids, for example, by selecting transgenic plants exhibiting an enhanced trait as compared to a control plant.

The above process can be repeated to produce multiple events of transgenic corn plants from cells that were transformed with recombinant DNA from the genes identified in Table 1. Progeny transgenic plants and seeds of the transformed plants were screened for the presence and single copy of the inserted nucleotide sequences set forth in Tables 1 and 2, and for increased water use efficiency, increased yield, increased nitrogen use efficiency, and altered phenotypes as shown in Tables 4-6 or Tables 7-12. From each group of multiple events of transgenic plants with a specific recombinant DNA from Table 1 the event(s) that showed increased yield, increased water use efficiency, increased nitrogen use efficiency, and altered phenotypes was (were) identified.

Example 2. Soybean Transformation

This example illustrates plant transformation in producing a transgenic soybean plant cell, plant, and seed having an enhanced trait, for example, increased water use efficiency, increased yield, increased nitrogen use efficiency, and altered phenotypes.

For *Agrobacterium* mediated transformation, soybean seeds were imbibed overnight and the meristem explants excised. Soybean explants were mixed with induced *Agrobacterium* cells containing plasmid DNA with the gene of interest cassette and a plant selectable marker cassette no later than 14 hours from the time of initiation of seed imbibition, and wounded using sonication. Following wounding, explants were placed in co-culture for 2-5 days at which point they were transferred to selection media to allow selection and growth of transgenic shoots. Resistant shoots were harvested in approximately 6-8 weeks and placed into selective rooting media for 2-3 weeks. Shoots producing roots were transferred to the greenhouse and potted in soil. Shoots that remained healthy on selection, but did not produce roots were transferred to non-selective rooting media for an additional two weeks. Roots from any shoots that produced roots off selection were tested for expression of the plant selectable marker before they were transferred to the greenhouse and potted in soil.

The above process can be repeated to produce multiple events of transgenic soybean plants from cells that were transformed with recombinant DNA from the genes identified in Table 1. Progeny transgenic plants and seed of the transformed plant cells were screened for the presence and single copy of the inserted gene, and for increased water use efficiency, increased yield, increased nitrogen use efficiency, and altered phenotypes.

Example 3. Canola Transformation

This example illustrates plant transformation in producing the transgenic canola plants of this disclosure and the production and identification of transgenic seed for transgenic canola having increased water use efficiency, increased yield, and increased nitrogen use efficiency.

Tissues from in vitro grown canola seedlings were prepared and inoculated with overnight-grown *Agrobacterium* cells containing plasmid DNA with a gene of interest cassette and a plant selectable marker cassette. Following co-cultivation with *Agrobacterium*, the infected tissues were allowed to grow on selection to promote growth of transgenic shoots, followed by growth of roots from the transgenic shoots. The selected plantlets were then transferred to the greenhouse and potted in soil. Molecular characterizations were performed to confirm the presence of the gene of interest, and its expression in transgenic plants and progenies. Progeny transgenic plants were selected from a population of transgenic canola events under specified growing conditions and were compared with control canola plants.

The above process can be repeated to produce multiple events of transgenic canola plants from cells that were transformed with recombinant DNA identified in Table 1and Table 2. Progeny transgenic plants and seed of the transformed plant cells were screened for the presence and single copy of the inserted gene or DNA, and for increased water use efficiency, increased yield, and increased nitrogen use efficiency. From each group of multiple events of transgenic plants with a specific recombinant DNA from Table 1 and Table 2 the event(s) that showed increased yield, increased water use efficiency, increased nitrogen use efficiency and altered phenotypes was (were) identified.

Example 4. Identification of Altered Phenotypes in Automated Greenhouse

This example illustrates screening and identification of transgenic plants for altered phenotypes in an automated greenhouse (AGH). The apparatus and the methods for automated phenotypic screening of plants are disclosed in US Patent Application Publication No. US 2011/0135161 A1, which is incorporated by reference herein in its entirety.

Screening and Identification of Transgenic Corn Plants for Altered Phenotypes.

Corn plants were tested in 3 screens in AGH under different conditions including non-stress, nitrogen deficit and water deficit stress conditions. All screens began with a non-stress condition during day 0-5 germination phase, after which the plants were grown for 22 days under screen specific conditions as shown in Table 3.

Water deficit is defined as a specific Volumetric Water Content (VWC) that is lower than the VWC of non-stress plant. For example, a non-stressed plant might be maintained at 55% VWC and water-deficit assay might be defined around 30% VWC as shown in Table 3. Data were collected using visible light and hyperspectral imaging as well as direct measurement of pot weight and amount of water and nutrient applied to individual plants on a daily basis.

Eight parameters were measured for each screen. The visible light color imaging based measurements are: biomass, canopy area and plant height. Biomass (B) is defined as estimated shoot fresh weight (g) of the plant obtained from images acquired from multiple angles of view. Canopy Area (Can) is defined as area of leaf as seen in top-down image ($mm^2$). Plant Height (H) refers to the distance from the top of the pot to the highest point of the plant derived from side image (mm). Anthocyanin score, chlorophyll score and water content score are hyperspectral imaging based parameters. Anthocyanin Score (An) is an estimate of anthocyanin content in the leaf canopy obtained from a top-down hyperspectral image. Chlorophyll Score (Chl) is a measurement of chlorophyll in the leaf canopy obtained from a top-down hyperspectral image. Water Content Score (WC) is a measurement of water in the leaf canopy obtained from a top-down hyperspectral image. Water Use Efficiency (WUE) is derived from the grams of plant biomass per liter of water added. Water Applied (WA) is a direct measurement of water added to a pot (pot with no hole) during the course of an experiment.

These physiological screen runs were set up so that tested transgenic lines were compared to a control line. The collected data were analyzed against the control using % delta and certain p-value cutoff. Tables 4-6 are summaries of transgenic corn plants comprising the disclosed recombinant DNA molecules with altered phenotypes under non stress, nitrogen deficit, and water deficit conditions, respectively.

"+" denotes an increase in the tested parameter at $p \leq 0.1$; whereas "−" denotes a decrease in the tested parameter at $p \leq 0.1$. The numbers in parenthesis show penetrance of the altered phenotypes, where the denominators represent total number of transgenic events tested for a given parameter in a specific screen, and the numerators represent the number of events showing a particular altered phenotype. For example, transgenic plants scored for anthocyanin content in the nitrogen limiting screens for TRDX2 SEQ ID NO: 6 and TRDX2 SEQ ID NO: 8 (Table 5), showed increased anthocyanin content at $p \leq 0.1$ under nitrogen deficit conditions.

TABLE 3

Description of the 3 AGH screens for corn plants.

| Screen | Description | Germination phase (5 days) | Screen specific phase (22 days) |
| --- | --- | --- | --- |
| Non-stress | well watered sufficient nitrogen | 55% VWC water | 55% VWC 8 mM nitrogen |
| Water deficit | limited nitrogen sufficient nitrogen | 55% VWC water | 30% VWC 8 mM nitrogen |

TABLE 3-continued

Description of the 3 AGH screens for corn plants.

| Screen | Description | Germination phase (5 days) | Screen specific phase (22 days) |
| --- | --- | --- | --- |
| Nitrogen deficit | well watered low nitrogen | 55% VWC water | 55% VWC 2 mM nitrogen |

TABLE 4

Summary of transgenic corn plants with altered phenotypes in AGH non-stress screens

| | Non-Stress | | | | | | | |
| --- | --- | --- | --- | --- | --- | --- | --- | --- |
| Gene_ID | An | B | Can | Chi | H | WA | WC | WUE |
| TRDX2-6 | | −(3/3) | −(1/3) | | | −(3/3) | | |
| TRDX2-10 | −(1/5) | −(4/5) | −(3/5) | −(1/5) | −(5/5) | −(5/5) | +(1/5) | −(4/5) |

TABLE 5

Summary of transgenic corn plants with altered phenotypes in AGH nitrogen deficit screens

| | Nitrogen Deficit | | | | | | | |
| --- | --- | --- | --- | --- | --- | --- | --- | --- |
| Gene_ID | An | B | Can | Chi | H | WA | WC | WUE |
| TRDX2-6 | +(1/3) | −(2/3) | −(3/3) | | −(1/3) | − (3/3) | −(1/3) | −(1/3) |
| TRDX2-8 | +(1/5) | | | −(2/5) | | − (3/5) | +(1/5) | +(3/5) |
| TRDX2-10 | | −(1/5) | −(3/5) | +(3/5) | −(3/5) | − (5/5) | | +(1/5) |

TABLE 6

Summary of transgenic corn plants with altered phenotypes in AGH water deficit screens

| | Water Deficit | | | | | | | |
| --- | --- | --- | --- | --- | --- | --- | --- | --- |
| Gene_ID | An | B | Can | Chi | H | WA | WC | WUE |
| TRDX2-6 | | −(2/3) | −(2/3) | −(2/3) | −(2/3) | −(2/3) | −(2/3) | −(2/3) |
| TRDX2-8 | −(2/5) | −(5/5) | −(5/5) | −(2/5) | −(5/5) | −(5/5) | −(3/5) | −(2/5) |
| TRDX2-10 | −(1/5) | +(1/5) | | +(3/5) | | | +(1/5) | +(1/5) |

Screening and Identification of Transgenic Soybean Plants for Altered Phenotypes.

Soybean plants were tested in 2 screens in AGH under non-stress and water deficit stress conditions. For non-stress screen, the plants were kept under constant VWC of 55% throughout the screen length of 27 days. For water deficit screen, the VWC was kept at 55% for the first 12 days after sowing, followed by gradual dry down at a rate of 0.025 VWC per day, followed by water recovery to 55% VWC at 25 days after sowing.

Water deficit is defined as a specific Volumetric Water Content (VWC) that is lower than the VWC of non-stress plant. For example, a non-stressed plant might be maintained at 55% VWC and water-deficit assay might be defined around 30% VWC as shown in Table 3. Data were collected using visible light and hyperspectral imaging as well as direct measurement of pot weight and amount of water and nutrient applied to individual plants on a daily basis.

Eight parameters were measured for each screen. The visible light color imaging based measurements are: biomass, canopy area and plant height. Biomass (B) is defined as estimated shoot fresh weight (grams) of the plant obtained from images acquired from multiple angles of view. Canopy Area (Can) is defined as area of leaf as seen in top-down image (mm²). Plant Height (H) refers to the distance from the top of the pot to the highest point of the plant derived from side image (mm). Chlorophyll score is a hyperspectral imaging based parameter. Chlorophyll Score (Chl) is a measurement of chlorophyll in the leaf canopy obtained from a top-down hyperspectral image. Water Use Efficiency (WUE) is derived from the grams of plant biomass per liter of water added. Water Applied (WA) is a direct measurement of water added to a pot (pot with no hole) during the course of an experiment.

These physiological screen runs were set up so that tested transgenic lines were compared to a control line. The collected data were analyzed against the control using % delta and/or certain p-value cutoff.

Example 5. Phenotypic Evaluation of Transgenic Plants for Increased Nitrogen Use Efficiency Corn nitrogen field efficacy trials were conducted to identify genes that can improve nitrogen use efficiency under nitrogen limiting conditions leading to increased yield performance as compared to non transgenic controls. A yield increase in corn can be manifested as one or more of the following: an increase in the number of ears per plant, an increase in the number of rows, number of kernels per row, kernel weight, thousand kernel weight, dry/wet ear length/diameter/weight, an increase in ear biomass, and increase in ear biomass per plot, an increase in the seed filling rate (which is the number of filled seeds divided by the total number of seeds and multiplied by 100), among others.

Table 7 provides a list of protein encoding DNA or polynucleotide sequence ("gene") for producing transgenic corn plant with increased nitrogen use efficiency as compared to a control plant. The element of Table 7 is described by reference to:

"SEQ ID NO: Polynucleotide" which identifies a nucleotide sequence.

"SEQ ID NO: Polypeptide" which identifies an amino acid sequence.

"Gene identifier" which refers to an arbitrary identifier.

"NUE results" which represents to the result of a nitrogen field trial for plants comprising a sequence in a construct with at least one event showing significant yield increase at p≤0.2 across locations. The first number refers to the number of events with significant yield increase, whereas the second number refers to the total number of events tested for each sequence in the construct.

TABLE 7

Recombinant DNA for increased nitrogen use efficiency in corn

| SEQ ID NO: Polynucleotide | SEQ ID NO: Polypeptide | Gene Identifier | NUE Results |
| --- | --- | --- | --- |
| 15 | 16 | TRDX2-8 | 1/5 |

Table 8 provides a nucleotide sequence for producing transgenic corn plant with increased nitrogen use efficiency as compared to a control plant. The suppression element of Table 8 is described by reference to:

"SEQ ID NO: Polynucleotide" which identifies a nucleotide sequence SEQ ID NO: 20 to suppress an endogenous target protein from corn;

"SEQ ID NO: Target Gene" which identifies a polynucleotide coding sequence from SEQ ID NO: 21 targeted for suppression.

"SEQ ID NO: Target Protein" which identifies an amino acid sequence from SEQ ID NO: 22.

"Gene identifier" which refers to an arbitrary identifier.

"NUE results" which refers to the sequence in a construct with at least one event showing significant yield increase at p≤0.2 across locations. The first number refers to the number of events with significant yield increase, whereas the second number refers to the total number of events tested for each sequence in the construct.

TABLE 8

Recombinant DNA for suppression of a target gene to provide increased nitrogen use efficiency in corn Table 8

| SEQ ID NO: Polynucleotide | SEQ ID NO: Target Gene | SEQ ID NO: Target Protein | Gene Identifier | NUE Results |
| --- | --- | --- | --- | --- |
| 20 | 21 | 22 | TRDX2-10 | 1/5 |

Example 6. Selection of Transgenic Plants with Increased Yield

This example illustrates selection and identification of transgenic plants for increased yield in both dicotyledonous and monocotyledonous plants with primary examples presented for corn, soybean, and canola in Tables 9-14 respectively.

Effective selection of increased and/or enhanced yielding transgenic plants uses hybrid progenies of the transgenic plants for corn, cotton, and canola, or inbred progenies of transgenic plants for soybean plants plant such as corn, cotton, canola, or inbred plant such as soy, canola and cotton over multiple locations with plants grown under optimal production management practices. An exemplary target for improved yield is a 2% to 10% increase in yield as compared to yield produced by plants grown from seed of a control plant. Selection methods can be applied in multiple and diverse geographic locations, for example up to 16 or more locations, over one or more planting seasons, for example at least two planting seasons, to statistically distinguish yield improvement from natural environmental effects.

Increased Yield in Corn

Table 9 provides a list of protein encoding DNA or polynucleotide sequence ("gene") in the production of transgenic corn plants with increased yield as compared to a control plant. The elements of Table 9 are described by reference to:

"SEQ ID NO: Polynucleotide" which identifies a nucleotide sequence.

"SEQ ID NO: Polypeptide" which identifies an amino acid sequence.

"Gene identifier" which refers to an arbitrary identifier.

"Broad acre yield results" represent results from broad acre yield field trial for plants comprising the sequence in constructs with at least one event showing significant yield increase at p≤0.2 across locations. The first number refers to the number of events with significant yield increase, whereas the second number refers to the total number of events tested for each sequence in a construct. As indicated in Table 9, genes TRDX2-2, TRDX2-3, TRDX2-4, TRDX2-5 and TRDX2-6 resulted in at least on significant positive events identified for increased yield. TRDX2-2, TRDX2-4, TRDX2-5, TRDX2-6 and TRDX2-8 resulted in positive broad acre yield increases in one broad acre yield trial. For example, as indicated in Table 9, gene TRDX2-3 was tested in two broad acre yield trials with 2 of 6 total events in trial 1 and 1 of 12 total events in trial 2 resulted in significantly positive yield compared to non-transgenic control plants.

TABLE 9

Recombinant DNA for increased yield in corn

| SEQ ID NO: Polynucleotide | SEQ ID NO: Polypeptide | Gene Identifier | Broad Acre Yield Results Trial 1 | Broad Acre Yield Results Trial 2 |
|---|---|---|---|---|
| 3 | 4 | TRDX2-2 | 1/8 | — |
| 5 | 6 | TRDX2-3 | 2/6 | 1/12 |
| 7 | 8 | TRDX2-4 | 1/6 | — |
| 9 | 10 | TRDX2-5 | 1/8 | — |
| 11 | 12 | TRDX2-6 | 2/8 | — |
| 15 | 16 | TRDX2-8 | 2/8 | — |

TABLE 10

Recombinant DNA for suppression of target genes for increased yield in corn

| SEQ ID NO: Polynucleotide | SEQ ID NO: Target Gene | SEQ ID NO: Target Protein | Gene Identifier | Broad Acre Yield Results |
|---|---|---|---|---|
| 17 | 18 | 19 | TRDX2-9 | 2/8 |
| 20 | 21 | 22 | TRDX2-10 | 1/6 |

Transgenic corn plants having increased yield are identified by screening using progenies of the transgenic plants over multiple locations for several years with plants grown under optimal production management practices and maximum weed and pest control. Selection methods can be applied in multiple and diverse geographic locations, for example up to 16 or more locations, over one or more planting seasons, for example at least two planting seasons, to statistically distinguish yield improvement from natural environmental effects.

A yield increase in corn can also be manifested as an increase in corn ear biomass which can be calculated on a per plant or per plot basis using a determination for weight per ear for any number of events in a plot compared to a control. This example illustrates the selection of a corn plant with increased yield measured as an increase in ear biomass.

Corn ear biomass was measured for plants grown under high planting density (52,000 plants per acre), nitrogen limiting conditions of 60 pounds (lbs) per acre or water limiting conditions (chronic drought condition).

A correction factor was applied to achieve a corrected plot ear biomass that was used to correct for ear biomass if there was a discrepancy in the number of plants per plot. To apply a corrected value to plot ear biomass, an estimate of plot ear biomass was measured in the full field trials, which was determined on a field by field location basis for plot ear biomass and stand. This analysis for ear biomass derived from the full field trials was used to calculate a correction factor that effectively reduced and accounted for the projected ear biomass per plot (fresh ear weight per plot basis). The factor for corrected ear biomass was applied to the plots and used to provide ear biomass per plot in the density, NUE and WUE trials.

The change or delta between transgenic events and non-transgenic control events for ear biomass in a plot was used to calculate a percent change for plot ear biomass.

"Corn ear biomass" was used as a parameter to predict increased yield for an individual event on a per plot basis. Table 11 presents events positive for corn ear biomass for plants comprising the sequences in constructs with at least one event showing significant increase in ear biomass or fresh weight per plot at a significant p≤0.2 across three locations. The ears were individually collected and ear biomass was measured by taking a fresh weight on the corn ear, which was the mass (grams) of the non-shelled whole ear (grain+cob) at measured at a physiological maturity stage of R6. Corn ear biomass per plot was used as an estimate of predicted yield increase in the field and was determined for each transgenic event in a construct as compared to non-transgenic wild-type control plants. The positive events for ear biomass are reported with the number of events with significant increase in ear biomass (first number N/N) compared to the total number of plants tested for each event (second number N/N). The field screens for density and NUE resulted in positive events which met the statistical criteria for significance across locations at p≤0.2 across three locations and are reported in Table 11.

Table 11 provides a reference to:

"SEQ ID NO: Polynucleotide" which identifies a nucleotide sequence.

"SEQ ID NO: Polypeptide" which identifies an amino acid sequence.

"Gene identifier" which refers to an arbitrary identifier.

"Event" which refers to an individual event for a given construct.

"Density" refers to a spacing of plants to estimate a field density of 52,000 plants per acre.

"NUE" refers to nitrogen use efficiency or increased yield under nitrogen limiting conditions of 60 pounds (lbs) nitrogen applied per acre.

TABLE 11

Recombinant DNA for increased corn ear biomass
[NS = non-statistically significant]

| SEQ ID NO: Polynucleotide | SEQ ID NO: Polypeptide | Gene Identifier | Event | Density | NUE |
|---|---|---|---|---|---|
| 3 | 4 | TRDX2-2 | 1 | NS | 2/4 |
| 3 | 4 | TRDX2-2 | 2 | NS | 2/4 |
| 7 | 8 | TRDX2-4 | 1 | 1/4 | 2/4 |
| 7 | 8 | TRDX2-4 | 2 | 1/4 | NS |
| 9 | 10 | TRDX2-5 | 1 | NS | 3/4 |
| 9 | 10 | TRDX2-5 | 2 | NS | 2/4 |
| 11 | 12 | TRDX2-6 | 1 | NS | 2/4 |
| 11 | 12 | TRDX2-6 | 2 | NS | 2/4 |
| 11 | 12 | TRDX2-6 | 3 | 3/4 | NS |

Table 12 provides a reference to:

"SEQ ID NO: Polynucleotide" which identifies a nucleotide sequence.

"SEQ ID NO: Target Gene" which identifies a nucleotide acid sequence.

"SEQ ID NO: Target Protein: which identifies an amino acid sequence

"Gene identifier" which refers to an arbitrary identifier.

"Event" which refers to an individual event for a given construct.

"Density" refers to a spacing of plants to estimate a field density of 52,000 plants per acre.

"NUE" refers to nitrogen use efficiency or increased yield under nitrogen limiting conditions of 60 pounds (lbs) nitrogen applied per acre.

"Corn ear biomass" was used as a parameter to predict increased yield for an individual event on a per plot basis. Table 12 presents events positive for corn ear biomass taken for plants comprising the sequences in constructs with at least one event showing significant increase in ear biomass or fresh weight per plot at a significant p≤0.2 across three locations. The ears were individually collected and ear biomass was measured by taking a fresh weight on the corn ear, which was the mass (grams) of the non-shelled whole ear (grain+cob) at measured at a physiological maturity stage of R6. Corn ear biomass per plot was used as an estimate of predicted yield increase in the field and was determined for each transgenic event in a construct as compared to non-transgenic wild-type control plants. The positive events for ear biomass are reported with the number of events with significant increase in ear biomass (first number N/N) compared to the total number of plants tested for each event (second number N/N). Only the high density screens that resulted in at least one positive event for corn ear biomass and met the statistical criteria at p≤0.2 across three locations and are reported in Table 12.

TABLE 12

Recombinant DNA for suppression of target genes for increased corn ear biomass

| SEQ ID NO: Poly-nucleotide | SEQ ID NO: Target Gene | SEQ ID NO: Target Protein | Gene Identifier | Event | Density |
|---|---|---|---|---|---|
| 20 | 21 | 22 | TRDX2-10 | 1 | 3/4 |

Increased Yield in Soybean

A yield increase in soybean can be manifested as one or more of the following: an increase in pods per plant, pods per acre, seeds per plant, seeds per pod, weight per seed, weight per pod, pods per node, number of nodes, and the number of internodes per plant.

Table 13 provides a list of protein encoding DNA or polynucleotide sequences used ("genes") in the production of transgenic soybean plants with increased yield as compared to a control plant. The elements of Table 13 are described by reference to:

"SEQ ID NO: Polynucleotide" which identifies a nucleotide sequence.

"SEQ ID NO: Polypeptide" which identifies an amino acid sequence.

"Gene identifier" which refers to an arbitrary identifier.

"Broad acre yield results" which refers to the sequence in a construct with at least one event showing significant yield increase at p≤0.2 across locations. The first number refers to the number of events with significant yield increase, whereas the second number refers to the total number of events tested for each sequence in a construct.

TABLE 13

Recombinant DNA for increased yield in soybean

| SEQ ID NO: Polynucleotide | SEQ ID NO: Polypeptide | Gene Identifier | Broad Acre Yield Results |
|---|---|---|---|
| 13 | 14 | TRDX2-7 | 1/7 |

Increased Yield in Canola

A yield increase in canola can be manifested as one or more of the following: an increase in silique number, number of siliques per plant, number of siliques per node, number of internodes, incidence of silique shatter, seeds per silique, seed weight per silique, improved seed, oil, or protein composition.

Table 14 provides a list of protein encoding DNA or polynucleotide sequences used ("genes") in the production of transgenic canola plants with increased yield as compared to a control plant. The element of Table 14 is described by reference to:

"SEQ ID NO: Polynucleotide" which identifies a nucleotide sequence.

"SEQ ID NO: Polypeptide" which identifies an amino acid sequence.

"Gene identifier" which refers to an arbitrary identifier.

"Broad acre yield results" which refers to the sequence in a construct with at least one event showing significant yield increase at p≤0.2 across locations. The first number refers to the number of events with significant yield increase, whereas the second number refers to the total number of events tested for each sequence in a construct.

TABLE 14

Recombinant DNA for increased Yield in Canola

| SEQ ID NO: Polynucleotide | SEQ ID NO: Polypeptide | Gene Identifier | Broad Acre Yield Results |
|---|---|---|---|
| 1 | 2 | TRDX2-1 | 3/8 |

Example 7. Suppression of Corn DWARF4 & DWARF4-Like Protein

This example illustrates the use of a suppression construct for use with RNA interference, for example, inverted repeats to suppress at least one DWARF4 and DWARF4-like protein from *Zea mays* (Zm.DWF4), which encodes a cytochrome P450 that was reported to mediate multiple 22alpha-hydroxylation steps in brassicosteroid biosynthesis expressed in actively growing tissues (Choe et al., 2001, *Plant J.* 26: 573-582). More specifically, this example illustrates the usage of a inverted repeats designed to target the gene from Zm.DWF4-like and suppress the Zm.DWF4-like protein in corn. Transgenic corn plants were stably transformed with inverted repeats and were used to suppress at least one Zm.DWF4-like protein and resulted in plants with an increased yield phenotype compared to control plants. In addition, this example provides methods for suppression using inverted repeats and a recombinant DNA construct with suppression elements of inverted repeats to suppress the Zm.DWF4-like protein for providing corn plants with increased yield, increased water use efficiency and increased nitrogen use efficiency.

In this embodiment, the Zm.DWF4-like protein in corn was suppressed using an inverted repeat comprising a sense and an antisense region. A specific example is provided by using SEQ ID NO: 17. The polynucleotide of SEQ ID NO: 17 encodes an antisense RNA molecule to target the complementary sense sequence. The RNA molecule is complementary, such that the RNA molecule is capable of forming a hairpin structure comprising a "sense" region and an "antisense" region. The regulatory RNA molecule provided by SEQ ID NO: 17 was designed to encode one or both strands of a double-stranded RNA molecule, such that one or both strands of a double-stranded RNA molecule can form a hairpin structure having a double-stranded region. In this example, the DNA molecule of SEQ ID NO: 17 was designed such that the sense and antisense regions are each about, but not limited to, 325 nucleotides in length. In another such embodiment, the loop region un-bound by the inverted repeats (Inverted Repeat 1 and Inverted Repeat 2) is about but not limited to 150 nucleotides in length. Following expression of such a RNA molecule, the sense and antisense regions of the inverted repeat form a double-stranded structure. The double-stranded region of the inverted repeat can be formed by two separate RNA strands, or by self-complementary portions of a single RNA having a hairpin structure and where one strand of the double-stranded region targets a region of the nucleic acid sequence of a Zm.DWF4-like gene and suppresses at least of protein, encoded by Zm.DWF4-like target gene.

A DNA molecule such as provided by SEQ ID NO: 17 that encodes an antisense RNA molecule to target the complementary sense sequence can also be designed to comprise a double-stranded region, wherein one strand of the double-stranded region is substantially identical (typically at least about 90%, 91%, 92%, 93%, 94%, 95%, 96%, 97%, 98%, 99%, 99.5%, 100% identical) in sequence to a nucleic acid sequence of a target gene, such as provided by SEQ ID NO: 18. The other strand of the double-stranded region is fully or partially complementary to the nucleic acid target from the target gene (typically at least about 90%, 91%, 92%, 93%, 94%, 95%, 96%, 97%, 98%, 99% or 99.5% identical to the complement of a region of the target nucleic acid). In another embodiment, the double-stranded region can be formed by two separate RNA strands, or by self-complementary portions of a single RNA having a hairpin structure and where one strand of the double-stranded region is identical to the target nucleic acid sequence over this region. In a non-limiting embodiment, this example can be used to suppress a protein if a target nucleic acid sequence is derived from a gene that is a member of a Zm.DWF4 or Zm.DWF4-like gene family, the sequence of the double-stranded region of a regulatory RNA molecule can be chosen with the aid of sequence comparison tools such that only the desired gene is down regulated. Alternatively, the inverted repeat sequence of a double-stranded region of a regulatory RNA molecule in this example can be used to down regulate a plurality of related genes that encode a Zm.DWF4 or Zm.DWF4-like protein simultaneously.

In a non-limiting embodiment, this example provides the nucleic acid sequence containing two inverted repeats in SEQ ID NO: 17, which was designed to a region of an mRNA derived from a target gene of SEQ ID NO: 18 encoding a corn Zm. DWF4-like protein SEQ ID NO: 19 and targeted to be down regulated. The use of nucleotide sequence of SEQ ID NO: 17 was used to target and suppress at least one of the Zm.DWF4 target gene in corn. The nucleic acid construct is provided, wherein the nucleic acid construct comprises (a) a first transcription unit comprising a polynucleotide operably linked to an constitutive promoter; (b) a second transcription unit comprising a selectable marker for example selectable marker genes conferring tolerance to spectinomycin; and (c) a pair of inverted repeats, wherein one of the inverted repeats is 5' of (a) and (b), and the other of the inverted repeats is 3' of (a) and (b). In one such embodiment, the corn Zm.DWF4 inverted repeats comprises a polynucleotide sequences presented in the 5' or 3' orientation to comprise a pair of inverted repeats as set forth as SEQ ID NO: 17, which may be used to suppress target gene sequence Zm.DWF4-like set forth as SEQ ID NO: 18. The inverted repeats used to suppress a corn Zm.DWF4-like target gene, for example, SEQ ID NO: 18, comprises the nucleic acid sequence of Inverted Repeat Configuration 1 (nucleotides 1-325 of SEQ ID NO:17) and Inverted Repeat Configuration 2 (nucleotides 486-800 of SEQ ID NO:17).

To construct transformation vectors for suppressing a target gene as identified as SEQ ID NO: 18, the amplified protein coding nucleotides are assembled in a sense and antisense arrangement and inserted into the base vector at the insertion site in the gene of interest expression cassette to provide a transcribed RNA molecule that will form a double-stranded RNA for RNA interference suppression of a target protein, such as provided as SEQ ID NO: 19 or a plurality of similar proteins. Inverted Repeat Configuration 1 & 2 are embedded in nucleic acid sequences used for the suppression of an endogenous corn Zm.DWF4-like target gene in corn such as set forth as SEQ ID NO: 17 (nucleotides 1-800). The target gene encoding a Corn DWF4-like protein set forth as SEQ ID NO: 18 (nucleotides 1-1527) was used to design the inverted repeats to suppress the corn DWF4-like protein set forth as SEQ ID NO: 19.

In the present example, the endogenous proteins that are targeted by suppression construct SEQ ID NO: 17 include but are not limited to Zm.DWF4-like proteins, for example SEQ ID NO: 22. Suppression of this endogenous Zm.DWF4-like protein resulted in increased yield relative to control plants lacking the transgene with at least one event showing significant yield increase at p≤0.2 across locations under standard field conditions (Table 10).

Example 8. Suppression of Ribozyme Inactivating Protein in Corn Plants

This example illustrates the use of an miRNAs to suppress ribozyme inactivating protein in corn. More specifically, it illustrates the use of a miRNA to suppress the expression of at least one target gene encoding a ribozyme inactivating protein (Zm.RIP), which a repressor of translation in corn plants. In this example, a transgene comprising the synthetic miRNA of SEQ ID NO: 20 was designed to suppress the expression of Zm.RIP in transgenic corn plants. Various other recombinant DNA constructs are available for use in suppressing the expression of a Zm.RIP target gene encoding the Zm.RIP protein in transgenic plants.

In this embodiment, the suppression approach for suppressing the expression of a Zm.RIP target protein include the use of a recombinant DNA construct that produces a synthetic miRNA that is designed to bind to a native or synthetic miRNA recognition site of the messenger RNA for the Zm.RIP target protein. Recombinant DNA constructs were used in transformation of a corn cell to produce multiple events that are each regenerated into transgenic corn plants, and further screened to identify the presence of the recombinant DNA construct containing the miRNA for Zm.RIP. For example, a recombinant DNA construct was used to deliver the miRNA set forth as SEQ ID NO: 20 to target the Zm.ZIP gene set forth as SEQ ID NO: 21 and suppress the expression of an endogenously expressed Zm. RIP protein, set forth as SEQ ID NO: 22.

The activity of the miRNA which suppresses an endogenous Zm.RIP protein was enhanced by enhancing the expression of the miRNA or by enhancing the ability of the miRNA to bind an RNA encoding a Zm.RIP target protein. A recombinant DNA encoding an RNA encoding the miRNA can be designed to enhance miRNA activity resulting in the enhanced suppression of the target mRNA and cognate protein, for example, Zm.RIP. Recombinant DNA encoding an RNA encoding a miRNA were designed using methods disclosed in US Patent Application Publication No. US 2009/0070898 A1.

The population of transgenic plants from multiple transgenic events were screened to identify the transgenic plants for the recombinant construct with SEQ ID NO: 20 and further screened for those transgenic events that exhibit enhanced yield. Suppression approaches using a recombinant DNA construct containing the suppression element of SEQ ID NO: 20 to suppress endogenously expressed Zm.RIP proteins, for example SEQ ID NO: 22 resulted in increased yield relative to control plants lacking the transgene with at least one event showing significant yield increase at $p \leq 0.2$ across locations under standard field conditions (Table 10). Additionally, suppression approaches using a recombinant DNA construct containing the suppression element of SEQ ID NO: 20 to suppress endogenously expressed Zm.RIP proteins in corn resulted in enhanced phenotypes such as increased chlorophyll and water content under non-stress, nitrogen deficit and water deficit conditions contributing to increased water use efficiency in transgenic corn with the Zm.RIP miRNA compared to non-transgenic control plants (Tables 4-6).

---

We claim:

1. A corn plant comprising a recombinant DNA molecule comprising a polynucleotide, wherein said polynucleotide comprises a nucleotide sequence encoding an inhibitory RNA molecule that targets a gene encoding a protein with at least 95% identity to SEQ ID NO: 22 to suppress expression of said protein, wherein said corn plant has at least one enhanced trait as compared to a control plant lacking said polynucleotide, wherein said enhanced trait is selected from the group consisting of increased yield, increased nitrogen use efficiency, and increased water use efficiency.

2. The corn plant of claim 1, wherein the recombinant DNA molecule further comprises a promoter that is operably linked to the polynucleotide, wherein said promoter is selected from the group consisting of a constitutive, inducible, tissue-specific, diurnally regulated, tissue enhanced, and cell-specific promoter.

3. The corn plant of claim 1, wherein said plant is a propagule selected from the group consisting of a cell, pollen, ovule, flower, embryo, leaf, root, stem, shoot, meristem, grain, and seed.

4. A method for increasing yield, increasing nitrogen use efficiency, or increasing water use efficiency in a corn plant comprising:
   a) crossing the corn plant of claim 1 with itself, a second plant from the same plant line, a wild type plant, or a second plant from a different line of plants to produce a seed;
   b) growing said seed to produce a plurality of progeny plants; and
   c) selecting a progeny plant comprising said recombinant DNA molecule having increased yield, increased nitrogen use efficiency, or increased water use efficiency relative to a plant not having said recombinant DNA molecule.

5. A method for increasing yield, increasing nitrogen use efficiency, or increasing water use efficiency in a corn plant comprising: expressing in a corn plant cell a recombinant DNA molecule comprising a nucleotide sequence encoding an inhibitory RNA molecule that targets a gene encoding a protein with at least 95% identity to SEQ ID NO: 22 to suppress expression of said protein; and growing a plant comprising said plant cell.

6. The corn plant of claim 1, wherein said polynucleotide comprises a nucleotide sequence that encodes an inhibitory RNA molecule that targets a gene encoding a protein with at least 99% identity to SEQ ID NO: 22.

7. The corn plant of claim 1, wherein said polynucleotide comprises a nucleotide sequence that encodes an inhibitory RNA molecule that targets a gene encoding a protein comprising the amino acid sequence as set forth in SEQ ID NO: 22.

8. The corn plant of claim 1, wherein said polynucleotide comprises a nucleotide sequence that has at least 90% identity to SEQ ID NO: 20.

9. The corn plant of claim 1, wherein said polynucleotide comprises a nucleotide sequence that has at least 95% identity to SEQ ID NO: 20.

10. The corn plant of claim 1, wherein said polynucleotide comprises a nucleotide sequence having the sequence as set forth in SEQ ID NO: 20.

11. The corn plant of claim 1, wherein said polynucleotide comprises a nucleotide sequence encoding an inhibitory RNA molecule that targets a gene with at least 90% identity to SEQ ID NO: 21.

12. The corn plant of claim 1, wherein said polynucleotide comprises a nucleotide sequence encoding an inhibitory RNA molecule that targets a gene with at least 95% identity to SEQ ID NO: 21.

13. The corn plant of claim 1, wherein said polynucleotide comprises a nucleotide sequence encoding an inhibitory RNA molecule that targets a gene comprising SEQ ID NO: 21.

14. The corn plant of claim 1, wherein said polynucleotide comprises a nucleotide sequence having at least 90% identity to SEQ ID NO: 21.

15. The corn plant of claim 1, wherein said polynucleotide comprises a nucleotide sequence having at least 95% identity to SEQ ID NO: 21.

16. The corn plant of claim 1, wherein said inhibitory RNA molecule is selected from the group consisting of a double-stranded RNA, an antisense RNA, an siRNA, and a transacting short interfering RNA (ta-siRNA).

17. The corn plant of claim 1, wherein said enhanced trait is increased yield.

18. The corn plant of claim 1, wherein said enhanced trait is increased nitrogen use efficiency.

19. The corn plant of claim 1, wherein said enhanced trait is increased water use efficiency.

\* \* \* \* \*

SEQUENCE LISTING

```
<160> NUMBER OF SEQ ID NOS: 29

<210> SEQ ID NO 1
<211> LENGTH: 504
<212> TYPE: DNA
<213> ORGANISM: Arabidopsis thaliana

<400> SEQUENCE: 1
atgatgaaca cgtacaacat ggtgaagcaa gaatttatca agaaatggat aaatactctc      60
cacatgttag attcttctat cgaacatcct ttgaacgtaa cggaaaggaa aaatgcgatt     120
agactatcat cggacttagc catggcagct gctcgaaatg gctctaccgt atggagccgc     180
gctcttattt ctaggagcgg aaataagaca gcaaacaaac ccatggcacg tcgaatacta     240
aaaaaagctc gaaatcggat gaagaaccgt tgtaacattc ttagacgaaa tggcaatttc     300
acggcgaaaa cctgggtgag aaaacgtacg gacttgctta agagtcttgt accgggaggt     360
gagttgatag acgacaaaga ttatttgata agagagacac ttgactacat tgtctatctc     420
cgagcacaag tggacgtcat gcgaaccgtc gcagccgtcg atttattcac ccgaaactta     480
accaacgatc gtaggaacaa ataa                                           504

<210> SEQ ID NO 2
<211> LENGTH: 167
<212> TYPE: PRT
<213> ORGANISM: Arabidopsis thaliana

<400> SEQUENCE: 2

Met Met Asn Thr Tyr Asn Met Val Lys Gln Glu Phe Ile Lys Lys Trp
1               5                   10                  15

Ile Asn Thr Leu His Met Leu Asp Ser Ser Ile Glu His Pro Leu Asn
            20                  25                  30

Val Thr Glu Arg Lys Asn Ala Ile Arg Leu Ser Ser Asp Leu Ala Met
        35                  40                  45

Ala Ala Ala Arg Asn Gly Ser Thr Val Trp Ser Arg Ala Leu Ile Ser
    50                  55                  60

Arg Ser Gly Asn Lys Thr Ala Asn Lys Pro Met Ala Arg Arg Ile Leu
65                  70                  75                  80

Lys Lys Ala Arg Asn Arg Met Lys Asn Arg Cys Asn Ile Leu Arg Arg
                85                  90                  95

Asn Gly Asn Phe Thr Ala Lys Thr Trp Val Arg Lys Arg Thr Asp Leu
            100                 105                 110

Leu Lys Ser Leu Val Pro Gly Gly Glu Leu Ile Asp Asp Lys Asp Tyr
        115                 120                 125

Leu Ile Arg Glu Thr Leu Asp Tyr Ile Val Tyr Leu Arg Ala Gln Val
    130                 135                 140
```

Asp Val Met Arg Thr Val Ala Ala Val Asp Leu Phe Thr Arg Asn Leu
145                 150                 155                 160

Thr Asn Asp Arg Arg Asn Lys
            165

<210> SEQ ID NO 3
<211> LENGTH: 1329
<212> TYPE: DNA
<213> ORGANISM: Arabidopsis thaliana

<400> SEQUENCE: 3

```
atggagccaa cgttccatgc ttttatgttt ccctggtttg cttttggtca tatgattcct      60
tttctacatc ttgcaaacaa actagctgag aaaggtcatc aaatcacttt cttgctacct     120
aagaaagccc aaaaacagtt ggaacatcac aatctgttcc cagacagtat tgtctttcac     180
cctctcacaa tccctcatgt caatggcctc cctgctggtg ctgagacaac ctcggatatc     240
tcaatctcga tggacaactt actgtcggaa gccttggatc tcactcgcga tcaggttgaa     300
gctgcggttc gtgctctgag accggacttg atcttttttg attttgctca ttggattcca     360
gaaattgcca agagcatat gatcaagagt gtgagttaca tgatagtatc tgcaacaaca     420
atagcttata catttgcccc tggtggtgta ttaggtgttc ccccaccagg ttatccttca     480
tcaaggtgt tgtaccgtga aaacgatgct catgccttag caaccttatc tatcttctat     540
aagagacttt atcatcagat cactacaggt tttaagagct gtgacatcat tgcattgagg     600
acatgtaatg aaatcgaagg taaattctgc gactatatat caagtcaata ccataagaag     660
gttctcttga ctggtccaat gctccctgag caagacacaa gtaaaccact agaagaacag     720
ttgagtcatt ttctgagcag gttcccaccg aggtcagtgg tgttttgtgc acttggtagc     780
cagatcgttc ttgaaaagga tcaattccaa gaactctgct tagggatgga gctgacaggt     840
ttaccgtttc ttatagcggt aaagccaccg agaggatcat cgacggtcga agaagggtta     900
ccagaagggt tccaggagcg ggtgaaaggg cgtggtgtgg ttttgggag atgggtgcaa     960
caaccattga tattggatca tccgtcaata ggctgctttg tgaaccattg tggtccggga    1020
acaatatggg agtgtcttat gactgattgt caaatggttt tgcttccatt tttaggtgat    1080
caagttctct tcacaagatt gatgaccgag gaattcaagg tgtctgtaga agtgtcgaga    1140
gaaaaaacag gatggttttc aaggagagc ttgagcgatg cgatcaagtc tgtgatggta    1200
aaagatagcg acctcggaaa gctagtgagg agtaaccacg ccaaattgaa ggagactctt    1260
ggtagtcatg gattattaac tggttacgtg gataaatttg tagaggaatt gcaagagtat    1320
ttgatttag                                                              1329
```

<210> SEQ ID NO 4
<211> LENGTH: 442
<212> TYPE: PRT
<213> ORGANISM: Arabidopsis thaliana

<400> SEQUENCE: 4

Met Glu Pro Thr Phe His Ala Phe Met Phe Pro Trp Phe Ala Phe Gly
1               5                   10                  15

His Met Ile Pro Phe Leu His Leu Ala Asn Lys Leu Ala Glu Lys Gly
            20                  25                  30

His Gln Ile Thr Phe Leu Leu Pro Lys Lys Ala Gln Lys Gln Leu Glu
        35                  40                  45

His His Asn Leu Phe Pro Asp Ser Ile Val Phe His Pro Leu Thr Ile

```
                50                  55                  60
Pro His Val Asn Gly Leu Pro Ala Gly Ala Glu Thr Thr Ser Asp Ile
 65                  70                  75                  80

Ser Ile Ser Met Asp Asn Leu Leu Ser Glu Ala Leu Asp Leu Thr Arg
                 85                  90                  95

Asp Gln Val Glu Ala Val Arg Ala Leu Arg Pro Asp Leu Ile Phe
                100                 105                 110

Phe Asp Phe Ala His Trp Ile Pro Glu Ile Ala Lys Glu His Met Ile
                115                 120                 125

Lys Ser Val Ser Tyr Met Ile Val Ser Ala Thr Thr Ile Ala Tyr Thr
                130                 135                 140

Phe Ala Pro Gly Gly Val Leu Gly Val Pro Pro Gly Tyr Pro Ser
145                 150                 155                 160

Ser Lys Val Leu Tyr Arg Glu Asn Asp Ala His Ala Leu Ala Thr Leu
                165                 170                 175

Ser Ile Phe Tyr Lys Arg Leu Tyr His Gln Ile Thr Thr Gly Phe Lys
                180                 185                 190

Ser Cys Asp Ile Ile Ala Leu Arg Thr Cys Asn Glu Ile Glu Gly Lys
                195                 200                 205

Phe Cys Asp Tyr Ile Ser Ser Gln Tyr His Lys Lys Val Leu Leu Thr
                210                 215                 220

Gly Pro Met Leu Pro Glu Gln Asp Thr Ser Lys Pro Leu Glu Glu Gln
225                 230                 235                 240

Leu Ser His Phe Leu Ser Arg Phe Pro Pro Arg Ser Val Val Phe Cys
                245                 250                 255

Ala Leu Gly Ser Gln Ile Val Leu Glu Lys Asp Gln Phe Gln Glu Leu
                260                 265                 270

Cys Leu Gly Met Glu Leu Thr Gly Leu Pro Phe Leu Ile Ala Val Lys
                275                 280                 285

Pro Pro Arg Gly Ser Ser Thr Val Glu Glu Gly Leu Pro Glu Gly Phe
                290                 295                 300

Gln Glu Arg Val Lys Gly Arg Gly Val Val Trp Gly Gly Trp Val Gln
305                 310                 315                 320

Gln Pro Leu Ile Leu Asp His Pro Ser Ile Gly Cys Phe Val Asn His
                325                 330                 335

Cys Gly Pro Gly Thr Ile Trp Glu Cys Leu Met Thr Asp Cys Gln Met
                340                 345                 350

Val Leu Leu Pro Phe Leu Gly Asp Gln Val Leu Phe Thr Arg Leu Met
                355                 360                 365

Thr Glu Glu Phe Lys Val Ser Val Glu Val Ser Arg Glu Lys Thr Gly
                370                 375                 380

Trp Phe Ser Lys Glu Ser Leu Ser Asp Ala Ile Lys Ser Val Met Asp
385                 390                 395                 400

Lys Asp Ser Asp Leu Gly Lys Leu Val Arg Ser Asn His Ala Lys Leu
                405                 410                 415

Lys Glu Thr Leu Gly Ser His Gly Leu Leu Thr Gly Tyr Val Asp Lys
                420                 425                 430

Phe Val Glu Glu Leu Gln Glu Tyr Leu Ile
                435                 440

<210> SEQ ID NO 5
<211> LENGTH: 672
<212> TYPE: DNA
<213> ORGANISM: Arabidopsis thaliana
```

<400> SEQUENCE: 5

```
atgactaaac agcacgcgaa ctggtctcct tacgataaca atggaggaac atgtgtggcc     60
atcgctggat cggattactg tgttatcgcc gccgatactc ggatgtctac tggttacagt    120
attcttagtc gcgattactc caaaatccat aaactagcgg acagagctgt tttgtcttcc    180
tctggcttcc aggctgatgt gaaagctttg cagaaggttc tcaaatccag acacttgatc    240
tatcaacatc agcataacaa gcagatgagc tgtcctgcaa tggcccagct tctctccaac    300
acgctttatt tcaagcggtt ttttccccta catgccttta atgttctagg agggcttgac    360
gaggaaggaa aagggtgtgt ctttacttac gacgctgttg gctcatacga gagagttgga    420
tacggtgctc aaggttctgg ttccacactc atcatgcctt ccttgacaa tcagctcaag     480
tctccaagtc ctcttttgct acctaaacag gattcaaaca cgccccttc cgaagctgaa     540
gcagttgact tggttaaaac tgttttcgca tctgccacag agagggatat ctacactgga    600
gacaagcttg agattatgat acttaaggcc gacggtatca agaccgaact catggacctg    660
aggaaagact aa                                                         672
```

<210> SEQ ID NO 6
<211> LENGTH: 223
<212> TYPE: PRT
<213> ORGANISM: Arabidopsis thaliana

<400> SEQUENCE: 6

```
Met Thr Lys Gln His Ala Asn Trp Ser Pro Tyr Asp Asn Asn Gly Gly
 1               5                  10                  15

Thr Cys Val Ala Ile Ala Gly Ser Asp Tyr Cys Val Ile Ala Ala Asp
                20                  25                  30

Thr Arg Met Ser Thr Gly Tyr Ser Ile Leu Ser Arg Asp Tyr Ser Lys
            35                  40                  45

Ile His Lys Leu Ala Asp Arg Ala Val Leu Ser Ser Gly Phe Gln
        50                  55                  60

Ala Asp Val Lys Ala Leu Gln Lys Val Leu Lys Ser Arg His Leu Ile
 65                  70                  75                  80

Tyr Gln His Gln His Asn Lys Gln Met Ser Cys Pro Ala Met Ala Gln
                85                  90                  95

Leu Leu Ser Asn Thr Leu Tyr Phe Lys Arg Phe Phe Pro Tyr Tyr Ala
            100                 105                 110

Phe Asn Val Leu Gly Gly Leu Asp Glu Glu Gly Lys Gly Cys Val Phe
        115                 120                 125

Thr Tyr Asp Ala Val Gly Ser Tyr Glu Arg Val Gly Tyr Gly Ala Gln
    130                 135                 140

Gly Ser Gly Ser Thr Leu Ile Met Pro Phe Leu Asp Asn Gln Leu Lys
145                 150                 155                 160

Ser Pro Ser Pro Leu Leu Leu Pro Lys Gln Asp Ser Asn Thr Pro Leu
                165                 170                 175

Ser Glu Ala Glu Ala Val Asp Leu Val Lys Thr Val Phe Ala Ser Ala
            180                 185                 190

Thr Glu Arg Asp Ile Tyr Thr Gly Asp Lys Leu Glu Ile Met Ile Leu
        195                 200                 205

Lys Ala Asp Gly Ile Lys Thr Glu Leu Met Asp Leu Arg Lys Asp
    210                 215                 220
```

<210> SEQ ID NO 7

<211> LENGTH: 1470
<212> TYPE: DNA
<213> ORGANISM: Saccharomyces cerevisiae

<400> SEQUENCE: 7

```
atgtccaatg ctgctttgca agtttatggc ggcgacgaag tttccgcagt agtcattgat      60
cctggctcat acacaacaaa tattggctat tcgggttctg acttccctca atcaattctg     120
ccctctgttt acggtaaata cactgcagat gaaggcaata agaaaatatt ttctgaacaa     180
tcaattggaa ttccaagaaa agattatgaa ctgaaaccta ttatcgagaa cggtctagtc     240
atagactggg ataccgcaca agaacagtgg caatgggcat tgcagaacga actctatttg     300
aattccaact ccggaatacc agctctgtta actgagcccg tttggaatag cacagaaaac     360
aggaaaaaat ctttagaagt gctcttagaa ggcatgcaat tgaagcctg ttacttagca      420
cccacatcga catgcgtttc ttttgcagca ggtagaccca attgtttggt tgttgatatt     480
ggacatgata cttgcagcgt cagtccaata gtggatggta tgacattatc aaagagtaca     540
agaagaaatt ttattgctgg gaaatttatc aatcacttga ttaaaaaggc attggaaccc     600
aaagaaatca taccactttt cgcaatcaag caaagaaaac cagagtttat aaaaaaaaca     660
ttcgactatg aggttgataa atcgctgtat gattacgcca ataaccgagg gttctttcaa     720
gagtgcaaag aaacactttg tcatatatgc ccaacaaaaa ctttggaaga acgaaaaca     780
gaattaagtt ctacggctaa aagatctatt gaaagtcctt ggaatgagga gattgttttt     840
gacaacgaaa ctcgttacgg ctttgctgaa gagcttttcc ttccaaaaga agatgacatc     900
ccagcaaatt ggcctcgctc gaactctgga gttgtgaaaa cttggcggaa tgattacgtg     960
ccgctaaaaa gaaccaagcc aagcggagtg aacaaatcag acaagaaagt tacaccaact    1020
gaagaaaagg aacaggaagc tgtaagcaaa tctacttctc cggctgcaaa tagtgcagac    1080
actccaaatg aaaccggtaa gagaccgtta aagaagaaa agcctcctaa agaaaataat     1140
gaattgattg gtctagcgga tcttgtttat tcgtctataa tgagcagtga tgtggatcta    1200
agagcgacac tagctcataa tgttgtcctt acaggcggta catcctctat tcctggatta    1260
agtgataggt taatgacaga actaaacaaa atactaccat ccccttaaatt tagaatatta   1320
acaacagggc acactatcga aaggcaatac cagtcatggc ttggcggtag tatacttaca    1380
agtctgggaa catttcacca actgtgggtt gggaaaaagg aatacgaaga ggtgggcgtc    1440
gaaagattgc ttaacgatag gtttagatag                                     1470
```

<210> SEQ ID NO 8
<211> LENGTH: 489
<212> TYPE: PRT
<213> ORGANISM: Saccharomyces cerevisiae

<400> SEQUENCE: 8

```
Met Ser Asn Ala Ala Leu Gln Val Tyr Gly Gly Asp Glu Val Ser Ala
1               5                   10                  15

Val Val Ile Asp Pro Gly Ser Tyr Thr Thr Asn Ile Gly Tyr Ser Gly
            20                  25                  30

Ser Asp Phe Pro Gln Ser Ile Leu Pro Ser Val Tyr Gly Lys Tyr Thr
        35                  40                  45

Ala Asp Glu Gly Asn Lys Lys Ile Phe Ser Glu Gln Ser Ile Gly Ile
    50                  55                  60

Pro Arg Lys Asp Tyr Glu Leu Lys Pro Ile Ile Glu Asn Gly Leu Val
65                  70                  75                  80
```

```
Ile Asp Trp Asp Thr Ala Gln Glu Gln Trp Gln Ala Leu Gln Asn
                85                  90                  95

Glu Leu Tyr Leu Asn Ser Asn Ser Gly Ile Pro Ala Leu Leu Thr Glu
            100                 105                 110

Pro Val Trp Asn Ser Thr Glu Asn Arg Lys Lys Ser Leu Glu Val Leu
            115                 120                 125

Leu Glu Gly Met Gln Phe Glu Ala Cys Tyr Leu Ala Pro Thr Ser Thr
    130                 135                 140

Cys Val Ser Phe Ala Ala Gly Arg Pro Asn Cys Leu Val Val Asp Ile
145                 150                 155                 160

Gly His Asp Thr Cys Ser Val Ser Pro Ile Val Asp Gly Met Thr Leu
                165                 170                 175

Ser Lys Ser Thr Arg Arg Asn Phe Ile Ala Gly Lys Phe Ile Asn His
            180                 185                 190

Leu Ile Lys Lys Ala Leu Glu Pro Lys Glu Ile Ile Pro Leu Phe Ala
    195                 200                 205

Ile Lys Gln Arg Lys Pro Glu Phe Ile Lys Lys Thr Phe Asp Tyr Glu
    210                 215                 220

Val Asp Lys Ser Leu Tyr Asp Tyr Ala Asn Asn Arg Gly Phe Phe Gln
225                 230                 235                 240

Glu Cys Lys Glu Thr Leu Cys His Ile Cys Pro Thr Lys Thr Leu Glu
                245                 250                 255

Glu Thr Lys Thr Glu Leu Ser Ser Thr Ala Lys Arg Ser Ile Glu Ser
                260                 265                 270

Pro Trp Asn Glu Glu Ile Val Phe Asp Asn Glu Thr Arg Tyr Gly Phe
    275                 280                 285

Ala Glu Glu Leu Phe Leu Pro Lys Glu Asp Asp Ile Pro Ala Asn Trp
    290                 295                 300

Pro Arg Ser Asn Ser Gly Val Val Lys Thr Trp Arg Asn Asp Tyr Val
305                 310                 315                 320

Pro Leu Lys Arg Thr Lys Pro Ser Gly Val Asn Lys Ser Asp Lys Lys
                325                 330                 335

Val Thr Pro Thr Glu Glu Lys Glu Gln Glu Ala Val Ser Lys Ser Thr
                340                 345                 350

Ser Pro Ala Ala Asn Ser Ala Asp Thr Pro Asn Glu Thr Gly Lys Arg
            355                 360                 365

Pro Leu Glu Glu Glu Lys Pro Pro Lys Glu Asn Asn Glu Leu Ile Gly
    370                 375                 380

Leu Ala Asp Leu Val Tyr Ser Ser Ile Met Ser Ser Asp Val Asp Leu
385                 390                 395                 400

Arg Ala Thr Leu Ala His Asn Val Val Leu Thr Gly Gly Thr Ser Ser
                405                 410                 415

Ile Pro Gly Leu Ser Asp Arg Leu Met Thr Glu Leu Asn Lys Ile Leu
            420                 425                 430

Pro Ser Leu Lys Phe Arg Ile Leu Thr Thr Gly His Thr Ile Glu Arg
    435                 440                 445

Gln Tyr Gln Ser Trp Leu Gly Gly Ser Ile Leu Thr Ser Leu Gly Thr
    450                 455                 460

Phe His Gln Leu Trp Val Gly Lys Lys Glu Tyr Glu Glu Val Gly Val
465                 470                 475                 480

Glu Arg Leu Leu Asn Asp Arg Phe Arg
                485
```

<210> SEQ ID NO 9
<211> LENGTH: 360
<212> TYPE: DNA
<213> ORGANISM: Arabidopsis thaliana

<400> SEQUENCE: 9

```
atggagaaat ctagagaaag cgagttcttg ttctgtaatt tgtgtgggac tatgcttgtc      60
ttgaaatcaa ccaagtatgc agaatgtcca cattgcaaaa caacacggaa tgcaaaagat     120
atcatcgaca aggaaatagc ttacacagtt tctgctgagg atatcagaag agaactagga     180
atatcattgt ttggtgaaaa aacgcaggca gaagctgagc taccaaagat caaaaaggca     240
tgcgagaaat gccagcatcc tgagcttgta tacacaacca gacagacgag atcagctgat     300
gaaggacaga caacatatta cacttgcccc aattgtgctc atagattcac agaaggttag     360
```

<210> SEQ ID NO 10
<211> LENGTH: 119
<212> TYPE: PRT
<213> ORGANISM: Arabidopsis thaliana

<400> SEQUENCE: 10

```
Met Glu Lys Ser Arg Glu Ser Glu Phe Leu Phe Cys Asn Leu Cys Gly
1               5                   10                  15

Thr Met Leu Val Leu Lys Ser Thr Lys Tyr Ala Glu Cys Pro His Cys
            20                  25                  30

Lys Thr Thr Arg Asn Ala Lys Asp Ile Ile Asp Lys Glu Ile Ala Tyr
        35                  40                  45

Thr Val Ser Ala Glu Asp Ile Arg Arg Glu Leu Gly Ile Ser Leu Phe
    50                  55                  60

Gly Glu Lys Thr Gln Ala Glu Ala Glu Leu Pro Lys Ile Lys Lys Ala
65                  70                  75                  80

Cys Glu Lys Cys Gln His Pro Glu Leu Val Tyr Thr Thr Arg Gln Thr
                85                  90                  95

Arg Ser Ala Asp Glu Gly Gln Thr Thr Tyr Tyr Thr Cys Pro Asn Cys
            100                 105                 110

Ala His Arg Phe Thr Glu Gly
        115
```

<210> SEQ ID NO 11
<211> LENGTH: 393
<212> TYPE: DNA
<213> ORGANISM: Arabidopsis thaliana

<400> SEQUENCE: 11

```
atggctctcg aatgggttgt gttaggttac gcagcagcag ctgaagcgat catggtgatt      60
ctcttgacga tgcctggact tgacgctctc cgcaaaggat tagtcgctgt aactcgtaat     120
ctcttgaaac cgtttctctc gataatcccg ttttgtctct tccttcttat ggatatttac     180
tggaagtatg agactcgacc ttcttgcgat ggtgattcgt gtactccttc tgagcatctt     240
cgtcaccaga atcgatcat gaagtctcag cgtaacgcgc ttctgattgc gtcggctctt      300
gttttctact ggattttgta ctctgtcacg aatttggttg tgaggattga gcagcttaat     360
cagagggttg agaggctcaa gaacaaggat tag                                   393
```

<210> SEQ ID NO 12
<211> LENGTH: 130
<212> TYPE: PRT
<213> ORGANISM: Arabidopsis thaliana

<400> SEQUENCE: 12

Met Ala Leu Glu Trp Val Val Leu Gly Tyr Ala Ala Ala Ala Glu Ala
1               5                   10                  15

Ile Met Val Ile Leu Leu Thr Met Pro Gly Leu Asp Ala Leu Arg Lys
            20                  25                  30

Gly Leu Val Ala Val Thr Arg Asn Leu Leu Lys Pro Phe Leu Ser Ile
        35                  40                  45

Ile Pro Phe Cys Leu Phe Leu Leu Met Asp Ile Tyr Trp Lys Tyr Glu
    50                  55                  60

Thr Arg Pro Ser Cys Asp Gly Asp Ser Cys Thr Pro Ser Glu His Leu
65              70                  75                  80

Arg His Gln Lys Ser Ile Met Lys Ser Gln Arg Asn Ala Leu Leu Ile
                85                  90                  95

Ala Ser Ala Leu Val Phe Tyr Trp Ile Leu Tyr Ser Val Thr Asn Leu
            100                 105                 110

Val Val Arg Ile Glu Gln Leu Asn Gln Arg Val Glu Arg Leu Lys Asn
        115                 120                 125

Lys Asp
    130

<210> SEQ ID NO 13
<211> LENGTH: 333
<212> TYPE: DNA
<213> ORGANISM: Pyropia yezoensis

<400> SEQUENCE: 13
atgaagaaga agctttcagt tcttttcact gttttagtt ttttgtaat aggtttcgca        60 caaattgctt ttgctgcaga tctagataat ggagaaaaag ttttttctgc taattgtgca     120
gcatgtcatg ctggcggtaa taacgccatt atgccagata aaaccttaaa aaagatgta     180 cttgaagcta atagtatgaa tactattgat gctattactt atcaagtaca aaatggtaaa     240
aatgccatgc ctgctttcgg aggtagactg gttgatgaag atattgaaga tgcagcaaat     300
tatgtattat ctcaatctga aaaggttgg tag                                   333

<210> SEQ ID NO 14
<211> LENGTH: 110
<212> TYPE: PRT
<213> ORGANISM: Pyropia yezoensis

<400> SEQUENCE: 14

Met Lys Lys Lys Leu Ser Val Leu Phe Thr Val Phe Ser Phe Val
1               5                   10                  15

Ile Gly Phe Ala Gln Ile Ala Phe Ala Ala Asp Leu Asp Asn Gly Glu
            20                  25                  30

Lys Val Phe Ser Ala Asn Cys Ala Ala Cys His Ala Gly Gly Asn Asn
        35                  40                  45

Ala Ile Met Pro Asp Lys Thr Leu Lys Lys Asp Val Leu Glu Ala Asn
    50                  55                  60

Ser Met Asn Thr Ile Asp Ala Ile Thr Tyr Gln Val Gln Asn Gly Lys
65              70                  75                  80

Asn Ala Met Pro Ala Phe Gly Gly Arg Leu Val Asp Glu Asp Ile Glu
                85                  90                  95

Asp Ala Ala Asn Tyr Val Leu Ser Gln Ser Glu Lys Gly Trp
            100                 105                 110

<210> SEQ ID NO 15
<211> LENGTH: 585
<212> TYPE: DNA
<213> ORGANISM: Zea mays

<400> SEQUENCE: 15

```
atggtcaccg ccaccacctc cccgctcttc tccctctcct ccctccgcgc ctccctccct      60
tcccccaccc gatttcacac gtctctctcg ctccgagccc tctccccacg tgctcgtctc     120
tctgccgccc tccctttcgc ctccccactc gtttcaggcg ggtacgggac ctgggcggcg     180
acttcaatct cgtccgcggg aaggttgaga cggcggggc tggaggtggt gtgcgaggcc      240
acgaccgggc ggcggccgga ctcggttaag aagagggagc gccagaacga caagcaccgc     300
atccgcaatc acgcgcgcaa ggccgagatg cgcactagga tgaaaaaggt cttaagagct     360
cttgaaaagc ttaggaagaa acctgacgcg cagcctgaag aaataattga gatagagaag     420
ctgatcgctg aggcatacaa agccatcgac aagacggtga aggttggcgc catgcatagg     480
aacacggcga accatcggaa gtctcgactg gcaaggagga agaaggccat cgagatactc     540
cgtggttggt atgtcccaaa cgctgaacct gtcgctgcca cctag                     585
```

<210> SEQ ID NO 16
<211> LENGTH: 194
<212> TYPE: PRT
<213> ORGANISM: Zea mays

<400> SEQUENCE: 16

```
Met Val Thr Ala Thr Thr Ser Pro Leu Phe Ser Leu Ser Ser Leu Arg
1               5                   10                  15

Ala Ser Leu Pro Ser Pro Thr Arg Phe His Thr Ser Leu Ser Leu Arg
            20                  25                  30

Ala Leu Ser Pro Arg Ala Arg Leu Ser Ala Ala Leu Pro Phe Ala Ser
        35                  40                  45

Pro Leu Val Ser Gly Gly Tyr Gly Thr Trp Ala Ala Thr Ser Ile Ser
    50                  55                  60

Ser Ala Gly Arg Leu Arg Arg Gly Leu Glu Val Val Cys Glu Ala
65                  70                  75                  80

Thr Thr Gly Arg Arg Pro Asp Ser Val Lys Lys Arg Glu Arg Gln Asn
                85                  90                  95

Asp Lys His Arg Ile Arg Asn His Ala Arg Lys Ala Glu Met Arg Thr
            100                 105                 110

Arg Met Lys Lys Val Leu Arg Ala Leu Glu Lys Leu Arg Lys Lys Pro
        115                 120                 125

Asp Ala Gln Pro Glu Glu Ile Ile Glu Ile Glu Lys Leu Ile Ala Glu
    130                 135                 140

Ala Tyr Lys Ala Ile Asp Lys Thr Val Lys Val Gly Ala Met His Arg
145                 150                 155                 160

Asn Thr Ala Asn His Arg Lys Ser Arg Leu Ala Arg Arg Lys Lys Ala
                165                 170                 175

Ile Glu Ile Leu Arg Gly Trp Tyr Val Pro Asn Ala Glu Pro Val Ala
            180                 185                 190

Ala Thr
```

<210> SEQ ID NO 17
<211> LENGTH: 800
<212> TYPE: DNA
<213> ORGANISM: artificial sequence
<220> FEATURE:

<223> OTHER INFORMATION: suppression element to target gene in Zea mays

<400> SEQUENCE: 17

```
gctcaattta gacgcccctc ttagcctttg tctcctagca atcaggagat gctcctcccg      60
gagttcttgc acggccttag ggcacccttc gaggaagaag atggcgaggg cgagcgccat     120
ggacgaagtc tcgtgccccg cgaagagcag gctcagcaag aggtccagga tctgttcctt     180
ggacaggttg gattgcttca gggcccatcc aagaaggtcg tcctcctcca cgcttgactt     240
ctccctgctc atcttctcaa gcctgccctc catcttcctc tctatcactc caagtatgga     300
cgcgcgtgac ttgagcgcct tccagaagta ctgcgatcgc gttaacgctt tatcacgata     360
ccttctacca catatcacta acaacatcaa cactcatcac tctcgacgac atccactcga     420
tcactactct cacacgaccg attaactcct catccacgcg gccgcctgca ggagcctgga     480
aggcgctcaa gtcacgcgcg tccatacttg gagtgataga gaggaagatg gagggcaggc     540
ttgagaagat gagcagggag aagtcaagcg tggaggagga cgaccttctt ggatgggccc     600
tgaagcaatc caacctgtcc aaggaacaga tcctggacct cttgctgagc ctgctcttcg     660
cggggcacga gcttcgtcc atggcgctcg ccctcgccat cttcttcctc gaagggtgcc     720
ctaaggccgt gcaagaactc cgggaggagc atctcctgat tgctaggaga caaaggctaa     780
gaggggcgtc taaattgagc                                                 800
```

<210> SEQ ID NO 18
<211> LENGTH: 1527
<212> TYPE: DNA
<213> ORGANISM: Zea mays

<400> SEQUENCE: 18

```
atgggcgcca tgatggcctc cataaccagc gagctcctct tcttccttcc cttcatcctg      60
ctggccctcc tcgccttgta caccaccacc gtcgccaaat gccacggcac ccacccgtgg     120
cgccgtcaga agaagaagcg gcccaacctg cccccgggcg cccgcggatg gcccttggtc     180
ggcgaaactt tcggctacct ccgcgcccac ccggccacct ccgtgggccg cttcatggag     240
cggcatgtcg cacggtacgg gaagatatac cggtcgagcc tgttcgggga gcggacggtg     300
gtgtcggcgg acgcggggct gaaccgctac atcctgcaga acgaggggcg gctgttcgag     360
tgcagctacc cgcgcagcat cggcggcatc ctgggcaagt ggtccatgct ggtgctcgtg     420
ggcgacgcgc accgcgagat gcgcgctatc tcgctcaact tcctcagctc cgtccgcctc     480
cgcgccgtgc tgctccccga ggtggagcgc acaccctgc tggtcctccg ctcgtggccg     540
ccctccgacg gcaccttctc cgcccagcac gaagccaaga agttcacgtt taacctgatg     600
gcgaagaaca taatgagcat ggaccccggc gaggaggaga cggagcggct gcggctggag     660
tacatcacct tcatgaaggg cgtcgtgtca gcgccgctca acttcccggg cacggcctac     720
tggaaggcgc tcaagtcgcg cgcgtccata cttggagtga tagagaggaa gatggaggac     780
aggcttgaga agatgagcag ggagaagtca agcgtggagg aggacgacct tcttggatgg     840
gccctgaagc aatccaacct gtccaaggaa cagatcctgg acctcttgct gagcctgctc     900
ttcgcggggc acgagacttc gtccatggcg ctcgccctcg ccatcttctt cctcgaaggg     960
tgccctaagg ccgtgcaaga actccgggag gagcatctcc tgattgctag agacaaagg    1020
ctaaggggg cgtccaaatt gagctgggaa gactacaagg aaatggtttt cacgcagtgt    1080
gttataaacg agacattgcg gctcggcaac gtggtcaggt tcctgcaccg gaaggtcatc    1140
cgagatgtac actacaatgg gtacgacata ccgcgggggt ggaaaatcct gccggttcta    1200
```

```
gcggcggtgc acctggactc gtcgctgtac gaggacccca gccggttcaa cccttggaga    1260
tggaagctgc agagcaacaa cgcgccaagc agcttcatgc cgtacggcgg cgggccgcgg    1320
ctgtgcgccg gtcggagct ggccaagctg gagatggcca tcttcctgca ccacctggtg     1380
ctcaacttcc ggtgggagct ggcggagccg gaccaggcct cgtctaccc tttcgtcgac      1440 ttccccaagg gcctcccgat cagggtccag cgggtcgccg acgaccaagg ccatcgtagc    1500
gttttgaccg agagcacaag aggctga                                         1527
```

<210> SEQ ID NO 19
<211> LENGTH: 508
<212> TYPE: PRT
<213> ORGANISM: Zea mays

<400> SEQUENCE: 19

```
Met Gly Ala Met Met Ala Ser Ile Thr Ser Glu Leu Leu Phe Phe Leu
1               5                   10                  15

Pro Phe Ile Leu Leu Ala Leu Leu Ala Leu Tyr Thr Thr Thr Val Ala
            20                  25                  30

Lys Cys His Gly Thr His Pro Trp Arg Arg Gln Lys Lys Lys Arg Pro
        35                  40                  45

Asn Leu Pro Pro Gly Ala Arg Gly Trp Pro Leu Val Gly Glu Thr Phe
    50                  55                  60

Gly Tyr Leu Arg Ala His Pro Ala Thr Ser Val Gly Arg Phe Met Glu
65                  70                  75                  80

Arg His Val Ala Arg Tyr Gly Lys Ile Tyr Arg Ser Ser Leu Phe Gly
                85                  90                  95

Glu Arg Thr Val Val Ser Ala Asp Ala Gly Leu Asn Arg Tyr Ile Leu
            100                 105                 110

Gln Asn Glu Gly Arg Leu Phe Glu Cys Ser Tyr Pro Arg Ser Ile Gly
        115                 120                 125

Gly Ile Leu Gly Lys Trp Ser Met Leu Val Leu Val Gly Asp Ala His
    130                 135                 140

Arg Glu Met Arg Ala Ile Ser Leu Asn Phe Leu Ser Ser Val Arg Leu
145                 150                 155                 160

Arg Ala Val Leu Leu Pro Glu Val Glu Arg His Thr Leu Leu Val Leu
                165                 170                 175

Arg Ser Trp Pro Pro Ser Asp Gly Thr Phe Ser Ala Gln His Glu Ala
            180                 185                 190

Lys Lys Phe Thr Phe Asn Leu Met Ala Lys Asn Ile Met Ser Met Asp
        195                 200                 205

Pro Gly Glu Glu Glu Thr Glu Arg Leu Arg Leu Glu Tyr Ile Thr Phe
    210                 215                 220

Met Lys Gly Val Val Ser Ala Pro Leu Asn Phe Pro Gly Thr Ala Tyr
225                 230                 235                 240

Trp Lys Ala Leu Lys Ser Arg Ala Ser Ile Leu Gly Val Ile Glu Arg
                245                 250                 255

Lys Met Glu Asp Arg Leu Glu Lys Met Ser Arg Glu Lys Ser Ser Val
            260                 265                 270

Glu Glu Asp Asp Leu Leu Gly Trp Ala Leu Lys Gln Ser Asn Leu Ser
        275                 280                 285

Lys Glu Gln Ile Leu Asp Leu Leu Ser Leu Leu Phe Ala Gly His
    290                 295                 300

Glu Thr Ser Ser Met Ala Leu Ala Leu Ala Ile Phe Phe Leu Glu Gly
```

```
                305                 310                 315                 320
Cys Pro Lys Ala Val Gln Glu Leu Arg Glu Glu His Leu Leu Ile Ala
                    325                 330                 335
Arg Arg Gln Arg Leu Arg Gly Ala Ser Lys Leu Ser Trp Glu Asp Tyr
                    340                 345                 350
Lys Glu Met Val Phe Thr Gln Cys Val Ile Asn Glu Thr Leu Arg Leu
                    355                 360                 365
Gly Asn Val Val Arg Phe Leu His Arg Lys Val Ile Arg Asp Val His
            370                 375                 380
Tyr Asn Gly Tyr Asp Ile Pro Arg Gly Trp Lys Ile Leu Pro Val Leu
385                 390                 395                 400
Ala Ala Val His Leu Asp Ser Ser Leu Tyr Glu Asp Pro Ser Arg Phe
                    405                 410                 415
Asn Pro Trp Arg Trp Lys Leu Gln Ser Asn Asn Ala Pro Ser Ser Phe
                    420                 425                 430
Met Pro Tyr Gly Gly Gly Pro Arg Leu Cys Ala Gly Ser Glu Leu Ala
                    435                 440                 445
Lys Leu Glu Met Ala Ile Phe Leu His His Leu Val Leu Asn Phe Arg
            450                 455                 460
Trp Glu Leu Ala Glu Pro Asp Gln Ala Phe Val Tyr Pro Phe Val Asp
465                 470                 475                 480
Phe Pro Lys Gly Leu Pro Ile Arg Val Gln Arg Val Ala Asp Asp Gln
                    485                 490                 495
Gly His Arg Ser Val Leu Thr Glu Ser Thr Arg Gly
            500                 505

<210> SEQ ID NO 20
<211> LENGTH: 1085
<212> TYPE: DNA
<213> ORGANISM: artificial sequence
<220> FEATURE:
<223> OTHER INFORMATION: suppression element to target gene in Zea mays

<400> SEQUENCE: 20
aggtagttga cggccgtggt catttcggca cggcccatgg tgacggtctc caggcccttc     60
ctgccgatga ggtcctggta ccggccgcca agccgagcc  acttggcgtt gtcgtcgagg    120
aggtgggtgt cgccgtcctt gccgaactcc caccacaccc cgccgggggt cctgaagccg    180
accaggtaga ggttgtccat acgtatggcg agcgtgatgg acctggtctt cgttttgagc    240
tcggtgtaga accagagctc ggggacattc ttctccagcg gcagcacggg ctggacgatg    300
cctgtatggt tggtgcagta tttgatcact tctttccgga cggaggtgat gaaggcgctg    360
taagggtagg ccgtgtcctc cacggggaag attcggtga  actttggcac tatattttc    420 ttctttgttt gagtaataag accactcaac tctgggtttg gctccgaagt actgcgatcg    480
cgttaacgct ttatcacgat accttctacc acatatcact aacaacatca acactcatca    540
ctctcgacga catccactcg atcactactc tcacacgacc gattaactcc tcatccacgc    600
ggccgcctgc aggagccgga gccaaaccca gagttgagtg gtcttattac tcaaacaaag    660
aagaaaaata tagtgccaaa gttcaccgaa atcttccccg tggaggacac ggcctaccct    720
tacagcgcct tcatcaccct cgtccggaaa gaagtgatca aatactgcac caaccataca    780
ggcatcgtcc agcccgtgct gccgctggag aagaatgtcc ccgagctctg gttctacacc    840
gagctcaaaa cgaagaccag gtccatcacg ctcgccatac gtatggacaa cctctacctg    900
gtcggcttca ggacccccgg cggggtgtgg tgggagttcg gcaaggacgg cgacacccac    960
```

```
ctcctcgacg acaacgccaa gtggctcggc tttggcggcc ggtaccagga cctcatcggc      1020
agtaagggcc tggagaccgt caccatgggc cgtgccgaaa tgaccacggc cgtcaactac      1080
cttag                                                                   1085
```

<210> SEQ ID NO 21
<211> LENGTH: 837
<212> TYPE: DNA
<213> ORGANISM: Zea mays

<400> SEQUENCE: 21

```
atggcggagc caaacccaga gttgagtggt cttattactc aaacaaagaa gaaaaatata       60
gtgccaaagt tcaccgaaat cttccccgtg gaggacacgg cctacccttä cagcgccttc      120 atcacctccg tccggaaaga agtgatcaaa tactgcacca accatacagg catcgtccag      180
cccgtgctgc cgctggagaa gaatgtcccc gagctctggt tctacaccga gctcaaaacg      240
aagaccaggt ccatcacgct cgccatacgt atggacaacc tctacctggt cggcttcagg      300 accccggcg gggtgtggtg ggagttcggc aaggacggcg acacccacct cctcgacgac      360
aacgccaagt ggctcggctt tggcggccgg taccaggacc tcatcggcag taagggcctg      420
gagaccgtca ccatgggccg tgccgaaatg accacggccg tcaactacct ggcgaagaag      480
acgacgacga cactagcaga ggcggcggag gaggaggagg agctgctgct gctgcaggca      540
gcggctgacc ccaaagccga ggagaagagc aacctggcga agctagtgat catggtatgc      600
gaggggctgc ggttcttcac cgtgtcccgc aaggtagacg aggggttcaa gaagccgcaa      660
gcggtgacca tatcggcgct ggaggggaag caggtgcaga atgggacag gatctcgaaa      720 gccgtcttca ggtgggccgt cgacccgacc gctgagatcc ccgacatgaa ggatcttggc      780
atcaaagata aaacgcagc agcgcagatc gttgcgctcg ttaaggacca aaactag        837
```

<210> SEQ ID NO 22
<211> LENGTH: 278
<212> TYPE: PRT
<213> ORGANISM: Zea mays

<400> SEQUENCE: 22

```
Met Ala Glu Pro Asn Pro Glu Leu Ser Gly Leu Ile Thr Gln Thr Lys
1               5                   10                  15

Lys Lys Asn Ile Val Pro Lys Phe Thr Glu Ile Phe Pro Val Glu Asp
            20                  25                  30

Thr Ala Tyr Pro Tyr Ser Ala Phe Ile Thr Ser Val Arg Lys Glu Val
        35                  40                  45

Ile Lys Tyr Cys Thr Asn His Thr Gly Ile Val Gln Pro Val Leu Pro
    50                  55                  60

Leu Glu Lys Asn Val Pro Glu Leu Trp Phe Tyr Thr Glu Leu Lys Thr
65                  70                  75                  80

Lys Thr Arg Ser Ile Thr Leu Ala Ile Arg Met Asp Asn Leu Tyr Leu
                85                  90                  95

Val Gly Phe Arg Thr Pro Gly Gly Val Trp Trp Glu Phe Gly Lys Asp
            100                 105                 110

Gly Asp Thr His Leu Leu Asp Asp Asn Ala Lys Trp Leu Gly Phe Gly
        115                 120                 125

Gly Arg Tyr Gln Asp Leu Ile Gly Ser Lys Gly Leu Glu Thr Val Thr
    130                 135                 140

Met Gly Arg Ala Glu Met Thr Thr Ala Val Asn Tyr Leu Ala Lys Lys
```

```
            145                 150                 155                 160
        Thr Thr Thr Thr Leu Ala Glu Ala Ala Glu Glu Glu Glu Leu Leu
                        165                 170                 175

Leu Leu Gln Ala Ala Ala Asp Pro Lys Ala Glu Glu Lys Ser Asn Leu
                        180                 185                 190

Ala Lys Leu Val Ile Met Val Cys Glu Gly Leu Arg Phe Phe Thr Val
                        195                 200                 205

Ser Arg Lys Val Asp Glu Gly Phe Lys Pro Gln Ala Val Thr Ile
                        210                 215                 220

Ser Ala Leu Glu Gly Lys Gln Val Gln Lys Trp Asp Arg Ile Ser Lys
        225                 230                 235                 240

Ala Val Phe Arg Trp Ala Val Asp Pro Thr Ala Glu Ile Pro Asp Met
                        245                 250                 255

Lys Asp Leu Gly Ile Lys Asp Lys Asn Ala Ala Ala Gln Ile Val Ala
                        260                 265                 270

Leu Val Lys Asp Gln Asn
                        275

<210> SEQ ID NO 23
<211> LENGTH: 223
<212> TYPE: PRT
<213> ORGANISM: Arabidopsis thaliana

<400> SEQUENCE: 23

Met Thr Lys Gln His Ala Asn Trp Ser Pro Tyr Asp Asn Asn Gly Gly
        1               5                   10                  15

Thr Cys Val Ala Ile Ala Gly Ser Asp Tyr Cys Val Ile Ala Ala Asp
                        20                  25                  30

Thr Arg Met Ser Thr Gly Tyr Ser Ile Leu Ser Arg Asp Tyr Ser Lys
                        35                  40                  45

Ile His Lys Leu Ala Asp Arg Ala Val Leu Ser Ser Gly Phe Gln
        50                  55                  60

Ala Asp Val Lys Ala Leu Gln Lys Val Leu Lys Ser Arg His Leu Ile
        65                  70                  75                  80

Tyr Gln His Gln His Asn Lys Gln Met Ser Cys Pro Ala Met Ala Gln
                        85                  90                  95

Leu Leu Ser Asn Thr Leu Tyr Phe Lys Arg Phe Phe Pro Tyr Tyr Ala
                        100                 105                 110

Phe Asn Val Leu Gly Gly Leu Asp Glu Glu Gly Lys Gly Cys Val Phe
                        115                 120                 125

Thr Tyr Asp Ala Val Gly Ser Tyr Glu Arg Val Gly Tyr Gly Ala Gln
                        130                 135                 140

Gly Ser Gly Ser Thr Leu Ile Met Pro Phe Leu Asp Asn Gln Leu Lys
        145                 150                 155                 160

Ser Pro Ser Pro Leu Leu Leu Pro Lys Gln Asp Ser Asn Thr Pro Leu
                        165                 170                 175

Ser Glu Ala Glu Ala Val Asp Leu Val Lys Thr Val Phe Ala Ser Ala
                        180                 185                 190

Thr Glu Arg Asp Ile Tyr Thr Val Asn Lys Leu Glu Ile Met Ile Leu
                        195                 200                 205

Lys Ala Asp Gly Ile Lys Thr Glu Leu Met Asp Leu Arg Lys Asp
                        210                 215                 220

<210> SEQ ID NO 24
<211> LENGTH: 489
```

<212> TYPE: PRT
<213> ORGANISM: Saccharomyces cerevisiae

<400> SEQUENCE: 24

```
Met Ser Asn Ala Ala Leu Gln Val Tyr Gly Gly Asp Glu Val Ser Ala
1               5                   10                  15

Val Val Ile Asp Pro Gly Ser Tyr Thr Thr Asn Ile Gly Tyr Ser Gly
            20                  25                  30

Ser Asp Phe Pro Gln Ser Ile Leu Pro Ser Val Tyr Gly Lys Tyr Thr
        35                  40                  45

Ala Asp Glu Gly Asn Lys Lys Ile Phe Ser Glu Gln Ser Ile Gly Ile
    50                  55                  60

Pro Arg Lys Asp Tyr Glu Leu Lys Pro Ile Ile Glu Asn Gly Leu Val
65                  70                  75                  80

Ile Asp Trp Asp Thr Ala Gln Glu Gln Trp Gln Trp Ala Leu Gln Asn
                85                  90                  95

Glu Leu Tyr Leu Asn Ser Asn Ser Gly Ile Pro Ala Leu Leu Thr Glu
            100                 105                 110

Pro Val Trp Asn Ser Thr Glu Asn Arg Lys Lys Ser Leu Glu Val Leu
        115                 120                 125

Leu Glu Gly Met Gln Phe Glu Ala Cys Tyr Leu Ala Pro Thr Ser Thr
130                 135                 140

Cys Val Ser Phe Ala Ala Gly Arg Pro Asn Cys Leu Val Val Asp Ile
145                 150                 155                 160

Gly His Asp Thr Cys Ser Val Ser Pro Ile Val Asp Gly Met Thr Leu
                165                 170                 175

Ser Lys Ser Thr Arg Arg Asn Phe Ile Ala Gly Lys Phe Ile Asn His
            180                 185                 190

Leu Ile Lys Lys Ala Leu Glu Pro Lys Glu Ile Ile Pro Leu Phe Ala
        195                 200                 205

Ile Lys Gln Arg Lys Pro Glu Phe Ile Lys Lys Thr Phe Asp Tyr Glu
    210                 215                 220

Val Asp Lys Ser Leu Tyr Asp Tyr Ala Asn Asn Arg Gly Phe Phe Gln
225                 230                 235                 240

Glu Cys Lys Glu Thr Leu Cys His Ile Cys Pro Thr Lys Thr Leu Glu
                245                 250                 255

Glu Thr Lys Thr Glu Leu Ser Thr Ala Lys Arg Ser Ile Glu Ser
            260                 265                 270

Pro Trp Asn Glu Glu Ile Val Phe Asp Asn Glu Thr Arg Tyr Gly Phe
        275                 280                 285

Ala Glu Glu Leu Phe Leu Pro Lys Glu Asp Ile Pro Ala Asn Trp
290                 295                 300

Pro Arg Ser Asn Ser Gly Val Val Lys Thr Trp Arg Asn Asp Tyr Val
305                 310                 315                 320

Pro Leu Lys Arg Thr Lys Pro Ser Gly Val Asn Lys Ser Asp Lys Lys
                325                 330                 335

Val Thr Pro Thr Glu Glu Lys Glu Gln Glu Ala Val Ser Lys Ser Thr
            340                 345                 350

Ser Pro Ala Ala Asn Ser Ala Asp Thr Pro Asn Glu Thr Gly Lys Arg
        355                 360                 365

Pro Leu Glu Glu Gly Lys Pro Pro Lys Glu Asn Asn Glu Leu Ile Gly
370                 375                 380

Leu Ala Asp Leu Val Tyr Ser Ser Ile Met Ser Ser Asp Val Asp Leu
385                 390                 395                 400
```

```
Arg Ala Thr Leu Ala His Asn Val Val Leu Thr Gly Gly Thr Ser Ser
                405                 410                 415

Ile Pro Gly Leu Ser Asp Arg Leu Met Thr Glu Leu Asn Lys Ile Leu
            420                 425                 430

Pro Ser Leu Lys Phe Arg Ile Leu Thr Thr Gly His Thr Ile Glu Arg
        435                 440                 445

Gln Tyr Gln Ser Trp Leu Gly Gly Ser Ile Leu Thr Ser Leu Gly Thr
    450                 455                 460

Phe His Gln Leu Trp Val Gly Lys Lys Glu Tyr Glu Glu Val Gly Val
465                 470                 475                 480

Glu Arg Leu Leu Asn Asp Arg Phe Arg
                485

<210> SEQ ID NO 25
<211> LENGTH: 130
<212> TYPE: PRT
<213> ORGANISM: Arabidopsis thaliana

<400> SEQUENCE: 25

Met Ala Leu Glu Trp Val Val Leu Gly Tyr Ala Ala Ala Ala Glu Ala
1               5                   10                  15

Ile Met Val Ile Leu Leu Thr Met Pro Gly Leu Asp Ala Leu Arg Lys
            20                  25                  30

Gly Leu Val Ala Val Thr Arg Asn Leu Leu Lys Pro Phe Leu Ser Ile
        35                  40                  45

Ile Pro Phe Cys Leu Phe Leu Leu Met Asp Ile Tyr Trp Lys Tyr Glu
    50                  55                  60

Thr Arg Pro Ser Cys Asp Gly Asp Ser Cys Thr Pro Ser Glu His Leu
65                  70                  75                  80

Arg His Gln Lys Ser Ile Met Lys Ser Gln Arg Asn Ala Leu Leu Ile
                85                  90                  95

Ala Ser Ala Leu Val Phe Tyr Trp Ile Leu Tyr Ser Val Thr Asn Leu
            100                 105                 110

Val Val Arg Ile Glu Gln Leu Asn Gln Arg Val Glu Arg Leu Lys Asn
        115                 120                 125

Lys Asn
    130

<210> SEQ ID NO 26
<211> LENGTH: 130
<212> TYPE: PRT
<213> ORGANISM: Arabidopsis lyrata

<400> SEQUENCE: 26

Met Ala Leu Glu Trp Val Val Leu Gly Tyr Ala Ala Ala Ala Glu Ala
1               5                   10                  15

Ile Met Val Ile Leu Leu Thr Met Pro Gly Leu Asp Ala Leu Arg Lys
            20                  25                  30

Gly Leu Val Ala Val Thr Arg Asn Leu Leu Lys Pro Phe Leu Ser Ile
        35                  40                  45

Ile Pro Phe Cys Leu Phe Leu Leu Met Asp Ile Tyr Trp Lys Tyr Glu
    50                  55                  60

Thr Arg Pro Ser Cys Asp Ser Asp Ser Cys Thr Pro Ser Glu His Leu
65                  70                  75                  80

Arg His Gln Lys Ser Ile Met Lys Ser Gln Arg Asn Ala Leu Leu Ile
                85                  90                  95
```

```
Ala Ser Ala Leu Val Phe Tyr Trp Ile Leu Tyr Ser Val Thr Asn Leu
            100                 105                 110

Val Val Arg Ile Glu Gln Leu Asn Gln Arg Val Glu Arg Leu Lys Asn
        115                 120                 125

Lys Asp
    130

<210> SEQ ID NO 27
<211> LENGTH: 110
<212> TYPE: PRT
<213> ORGANISM: Porphyra tenera

<400> SEQUENCE: 27

Met Lys Lys Lys Phe Ser Val Leu Phe Thr Val Phe Ser Phe Phe Val
1               5                   10                  15

Ile Gly Phe Ala Gln Ile Ala Phe Ala Ala Asp Leu Asp Asn Gly Glu
            20                  25                  30

Lys Val Phe Ser Ala Asn Cys Ala Ala Cys His Ala Gly Gly Asn Asn
        35                  40                  45

Ala Ile Met Pro Asp Lys Thr Leu Lys Lys Asp Val Leu Glu Ala Asn
    50                  55                  60

Ser Met Asn Thr Ile Asp Ala Ile Thr Tyr Gln Val Gln Asn Gly Lys
65                  70                  75                  80

Asn Ala Met Pro Ala Phe Gly Gly Arg Leu Val Asp Glu Asp Ile Glu
                85                  90                  95

Asp Ala Ala Asn Tyr Val Leu Ser Gln Ser Glu Lys Gly Trp
            100                 105                 110

<210> SEQ ID NO 28
<211> LENGTH: 194
<212> TYPE: PRT
<213> ORGANISM: Zea mays

<400> SEQUENCE: 28

Met Val Thr Ala Thr Thr Ser Pro Leu Phe Ser Leu Ser Ser Leu Arg
1               5                   10                  15

Ala Ser Leu Pro Ser Pro Thr Arg Phe His Thr Ser Leu Ser Leu Arg
            20                  25                  30

Ala Leu Ser Pro Arg Ala Arg Leu Ser Ala Ala Leu Pro Phe Ala Ser
        35                  40                  45

Pro Leu Val Ser Gly Gly Tyr Gly Thr Trp Ala Ala Thr Ser Ile Ser
    50                  55                  60

Ser Ala Gly Arg Leu Arg Arg Gly Leu Glu Val Val Cys Glu Ala
65                  70                  75                  80

Thr Thr Gly Arg Arg Pro Asp Ser Val Lys Lys Arg Glu Arg Gln Asn
                85                  90                  95

Asp Lys His Arg Ile Arg Asn His Ala Arg Lys Ala Glu Met Arg Thr
            100                 105                 110

Arg Met Lys Lys Val Leu Arg Ala Leu Glu Lys Leu Arg Lys Lys Pro
        115                 120                 125

Asp Ala Gln Pro Glu Glu Ile Ile Glu Ile Glu Lys Leu Ile Ala Glu
    130                 135                 140

Ala Tyr Lys Ala Ile Asp Lys Thr Val Lys Val Gly Ala Met His Arg
145                 150                 155                 160

Asn Thr Ala Asn His Arg Lys Ser Arg Leu Ala Arg Arg Lys Lys Ala
                165                 170                 175
```

Ile Glu Ile Leu Arg Gly Trp Tyr Val Pro Asn Ala Glu Pro Val Ala
            180                 185                 190

Ala Thr

<210> SEQ ID NO 29
<211> LENGTH: 193
<212> TYPE: PRT
<213> ORGANISM: Zea mays

<400> SEQUENCE: 29

Met Val Thr Ala Thr Thr Ser Pro Leu Phe Ser Leu Ser Ser Leu Arg
1               5                   10                  15

Ala Ser Leu Pro Ser Pro Thr Arg Phe His Thr Ser Leu Ser Leu Arg
            20                  25                  30

Ala Leu Ser Pro Arg Ala Arg Leu Ser Ala Ser Leu Pro Phe Ala Ser
            35                  40                  45

Pro Leu Val Ser Gly Gly Tyr Gly Thr Trp Ala Ala Thr Ser Val Ser
        50                  55                  60

Ser Ala Gly Arg Leu Arg Arg Gly Leu Glu Val Val Cys Glu Ala
65                  70                  75                  80

Thr Thr Gly Arg Arg Pro Asp Ser Val Lys Lys Arg Glu Arg Gln Asn
                85                  90                  95

Asp Lys His Arg Ile Arg Asn His Ala Arg Lys Ala Glu Met Arg Thr
            100                 105                 110

Arg Met Lys Lys Val Leu Arg Ala Leu Glu Lys Leu Arg Lys Lys Pro
            115                 120                 125

Asp Ala Gln Pro Glu Glu Ile Ile Glu Ile Glu Lys Leu Ile Ala Glu
        130                 135                 140

Ala Tyr Lys Ala Ile Asp Lys Thr Val Lys Val Gly Ala Met His Arg
145                 150                 155                 160

Asn Thr Ala Asn His Arg Lys Ser Arg Leu Ala Arg Arg Lys Lys Ala
                165                 170                 175

Ile Glu Ile Leu Arg Gly Trp Tyr Val Pro Asn Ala Glu Pro Val Ala
            180                 185                 190

Ala